(12) United States Patent
Ueno

(10) Patent No.: US 9,824,192 B2
(45) Date of Patent: Nov. 21, 2017

(54) SIMULATION METHOD FOR MACROMOLECULAR MATERIAL

(71) Applicant: SUMITOMO RUBBER INDUSTRIES, LTD., Kobe-shi, Hyogo (JP)

(72) Inventor: Shinichi Ueno, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 825 days.

(21) Appl. No.: 14/220,240

(22) Filed: Mar. 20, 2014

(65) Prior Publication Data

US 2014/0303945 A1    Oct. 9, 2014

(30) Foreign Application Priority Data

Apr. 4, 2013  (JP) ................. 2013-078832
Apr. 15, 2013 (JP) ................. 2013-085078
Apr. 15, 2013 (JP) ................. 2013-085079

(51) Int. Cl.
G06G 7/58      (2006.01)
G06F 19/00     (2011.01)
G06F 17/50     (2006.01)

(52) U.S. Cl.
CPC ........ G06F 19/701 (2013.01); G06F 17/5009 (2013.01); G06F 19/704 (2013.01); G06F 17/5095 (2013.01)

(58) Field of Classification Search
CPC .................................................. G06F 17/5009

USPC .......................................................... 703/12
See application file for complete search history.

(56) References Cited

FOREIGN PATENT DOCUMENTS

JP       2012-238168 A    12/2012

OTHER PUBLICATIONS

Abrams: Inhomogeneous Coarse-Graining of Polymers and Polymer/Metal Interfaces; Computational Soft Matter: From Synthetic Polymers to Proteins, Lecture Notes; NIC Series, vol. 23, pp. 275-288, 2004.*
Auhl et al.: Equilibration of long chain polymer melts in computer simulations; Journal of Chemical Physics vol. 119, No. 24; 12 pp.; 2003.*
Sliozberg et al.: Preparation of Entangled Polymer Melts of Various Architecture for Coarse-grained Models; ARL-TR-5679; Sep. 2011; 26 pp.*

(Continued)

*Primary Examiner* — Hugh Jones
(74) *Attorney, Agent, or Firm* — Birch, Stewart, Kolasch & Birch, LLP

(57) ABSTRACT

A computer simulation method for a macromolecular material and filler is disclosed, wherein a polymer model of a macromolecular chain of the macromolecular material and a filler model of the filler are defined; and a molecular dynamics calculation is performed using the filler model and the polymer models disposed in a space in order to compute the thickness of an interface layer between the filler and the macromolecular material. To compute the thickness, the space is partitioned into domains bounded by boundary surfaces; relaxation moduli of the domains are computed; and based on a variation of the relaxation moduli of the domains, the thickness of the interface layer is computed.

20 Claims, 22 Drawing Sheets

(56) References Cited

OTHER PUBLICATIONS

Senda et al.: Fast convergence to equilibrium for long-chain polymer melts using a MD/ continuum hybrid method; arXiv: 1205.6582v1; May 2012; 13 pp.*

Liu et al.: Polymer—nanoparticle interfacial behavior revisited: A molecular dynamics study; Phys. Chem. Chem. Phys., 2011, 13, 13058-13069.*

Arrighi et al., "The glass transition and interfacial layer in styrene-butadiene rubber containing silica nanofiller," Polymer (2003), vol. 44, pp. 6259-6266.

Barbier et al., "Interface Between End-Functionalized PEO Oligomers and a Silica Nanoparticle Studied by Molecular Dynamics Simulations," Macromolecules (2004), vol. 37, pp. 4695-4710.

Brown et al., "Effect of Filler Particle Size on the Properties of Model Nanocomposites," Macromolecules (2008), vol. 41, pp. 1499-1511.

Extended European Search Report issued Jul. 7, 2014, in European Patent Application No. 14161843.9, 9 pp.

Fragiadakis et al., "Glass transition and molecular dynamics in poly(dimethylsiloxane)/silica nanocomposites," Polymer (2005), vol. 46, pp. 6001-6008.

Ghanbari et al., "Interphase Structure in Silica—Polystyrene Nanocomposites: A Coarse-Grained Molecular Dynamics Study," Macromolecules (2012), vol. 45, pp. 572-584.

Hamandaris, V. A., "Atomistic Molecular Dynamics Simulations of Polymer Melt Viscoelasticity," PhD Thesis, 2001, pp. 1-197, Patras Greece.

Hu et al., "Molecular dynamics simulation of interfacial thermal conductance between silicon and amorphous polyethylene," Applied Physics Letters (2007), vol. 91, pp. 241910-1-241910-3.

Klonos et al., "Comparative studies on effects of silica and titania nanoparticles on crystallization and complex segmental dynamics in poly(dimethylsiloxane)," Polymer (2010), vol. 51, pp. 5490-5499.

Ndoro et al., "Interface of Grafted and Ungrafted Silica Nanoparticles with a Polystyrene Matrix: Atomistic Molecular Dynamics Simulations," Macromolecules (2011), vol. 44, 2316-2327.

* cited by examiner

SIMULATION METHOD FOR MACROMOLECULAR MATERIAL

BACKGROUND OF THE INVENTION

The present invention relates to a computer simulation method for a macromolecular material and filler, more particularly to a method for computing the thickness of an interface layer formed between the macromolecular material and the filler.

In recent years, in order to develop or design macromolecular materials such as rubber compounds, there have been proposed computer simulation methods in which various conditions such as the structure of the macromolecular material and the blending ratio of filler can be incorporated into the simulation calculation, and thereby it is possible to obtain a material property without experimentally actually producing the macromolecular material with the filler.

In the meantime, when filler is blended into a macromolecular material, as shown in FIG. 10, around the filler particles or aggregation of the filler, there is formed an interface layer (in some cases, called glass layer) having different dynamic properties than the macromolecular material itself so called bulk.

In a conventional simulation method, the thickness of such interface layer is obtained through an experimental measurement using the macromolecular material and the filler and the obtained thickness value is input in a computer before computing material properties of the macromolecular material with the filler. Accordingly, much time and cost are required for the experimental measurement.

SUMMARY OF THE INVENTION

It is therefore, an object of the present invention to provide a simulation method for a macromolecular material and filler in which, in a system in which filler and a macromolecular material exist together, the thickness of the interface layer therebetween can be computed.

According to the present invention, a simulation method for a macromolecular material and filler, comprises:

a process in which a polymer model of a macromolecular chain of the macromolecular material modeled by a plurality of particle models is defined, a process in which a filler model of at least an outer surface of the filler is defined, a simulation process in which a molecular dynamics calculation is performed using the filler model and the polymer models disposed in a space, an interface-layer-thickness calculation process in which, the thickness of an interface layer formed between the filler and the bulk of the macromolecular material and having a dynamic property different than that of the bulk, is computed from results of the simulation process, wherein the interface-layer-thickness calculation process comprises a process in which the space in which the polymer models are disposed is partitioned into a plurality of domains bounded by boundary surfaces along said outer surface of the filler, a relaxation modulus calculation process in which relaxation moduli of the domains are computed, and a determining process in which the thickness of the interface layer is computed based on a variation of the relaxation moduli of the domains.

In the above-mentioned simulation method according to the present invention, the polymer model can be an all-atom model or a united-atom model of the macromolecular chain.

Further, the polymer model can be a coarse-grained model of the macromolecular chain modeled by a plurality of beads, therefore, the particle models are the beads.

When the polymer model is the coarse-grained model, a potential between two particle models which can exert a repulsive force between the particle models which increases to infinity as the distance between the particle models decreases, can be defined between the particle models of the polymer models. In this case, the potential can be defined by the following expression:

$$R = \begin{cases} 4\varepsilon\left[\left(\dfrac{\sigma}{r_{ij}}\right)^{12} - \left(\dfrac{\sigma}{r_{ij}}\right)^{6} + \dfrac{1}{4}\right] & \text{if } r_{ij} < 2^{\frac{1}{6}}\sigma \\ 0 & \text{if } r_{ij} \geq 2^{\frac{1}{6}}\sigma \end{cases}$$

wherein $r_{ij}$ is the distance between two beads, $\varepsilon$ is a coefficient relating to the intensity of the repulsive force potential R, and $\sigma$ is a coefficient relating to the distance within which the repulsive force potential R exerts.

Further, when the polymer model is the coarse-grained model, a repulsive force potential between two particle models which can exert a repulsive force between the particle models which increases up to a finite value as the distance between the particle models decreases, can be defined between the particle models of the polymer models. In this case, the repulsive force potential can be defined by the following expression:

$$R = \begin{cases} \dfrac{1}{2}\left[a_{ij}\left(1 - \dfrac{r_{ij}}{r_c}\right)^{2}\right] & \text{if } r_{ij} < r_c \\ 0 & \text{if } r_{ij} \geq r_c \end{cases}$$

wherein $r_{ij}$ is the distance between the particle models, $a_{ij}$ is a coefficient relating to the intensity of the repulsive force, and $r_c$ is a cutoff distance.

DESCRIPTION OF THE PREFERRED EMBODIMENTS

Embodiments of present invention will now be described in detail in conjunction with the accompanying drawings.

In each of the following embodiments of the present invention, the simulation method for a macromolecular material and filler is used to analyze reactions between the macromolecular material and the filler mixed therein by the use of a computer.

Figure 1:
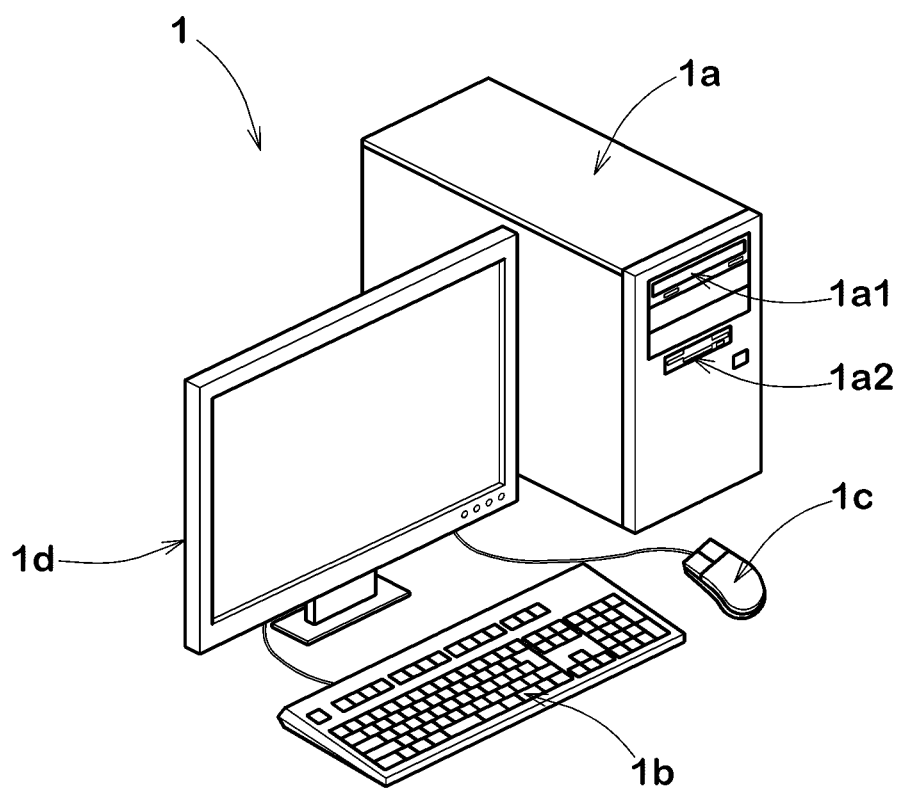
FIG. 1 is a perspective view of a computer implementing a simulation method according to the present invention.

As shown in FIG. 1 for example, the computer 1 comprises a main body 1a, a keyboard 1b, a mouse 1c and a display 1d. The main body 1a comprises an arithmetic processing unit (CPU), memory, storage devices such as magnetic disk, disk drives 1a1 and 1a2 and the like. In the storage device, programs/software for carrying out the simulating method are stored.

Here, the term "macromolecular material" encompasses rubber, a resin, an elastomer and the like.

The term "filler" encompasses powdery materials, e.g. carbon black, silica, alumina and the like.

Figure 2:
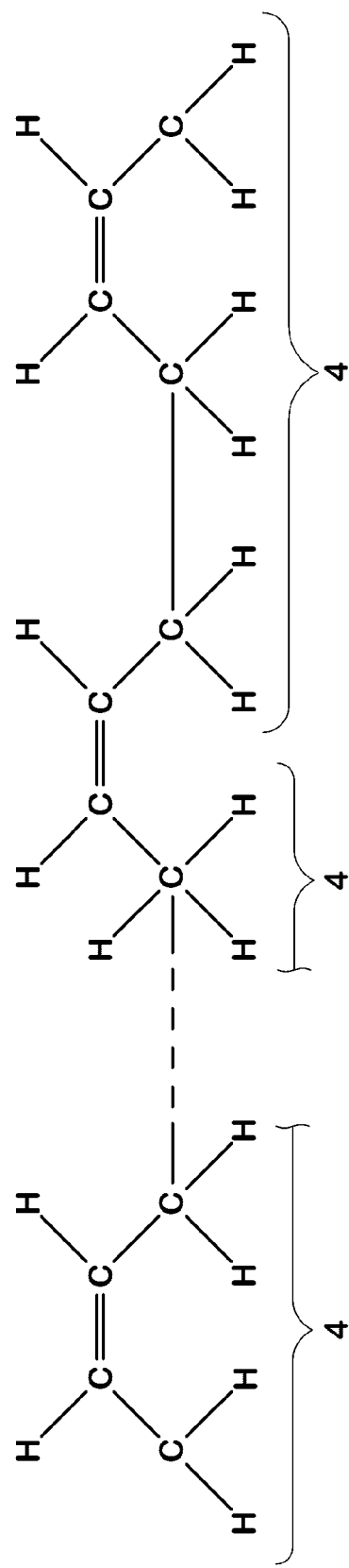
FIG. 2 is a the structural formula of cis-1,4 polybutadiene as an example of the macromolecular material.

FIG. 2 shows an example of the macromolecular material which is cis-1,4 polybutadiene (hereinafter simply, the polybutadiene). The macromolecular chain constituting the polybutadiene is formed from monomers {—[CH2—CH=CH—CH2]-} each of which is made up of a methylene group (—CH2-) and a methine group (—CH—) and which are bound at a polymerization degree (n).

Figure 3:
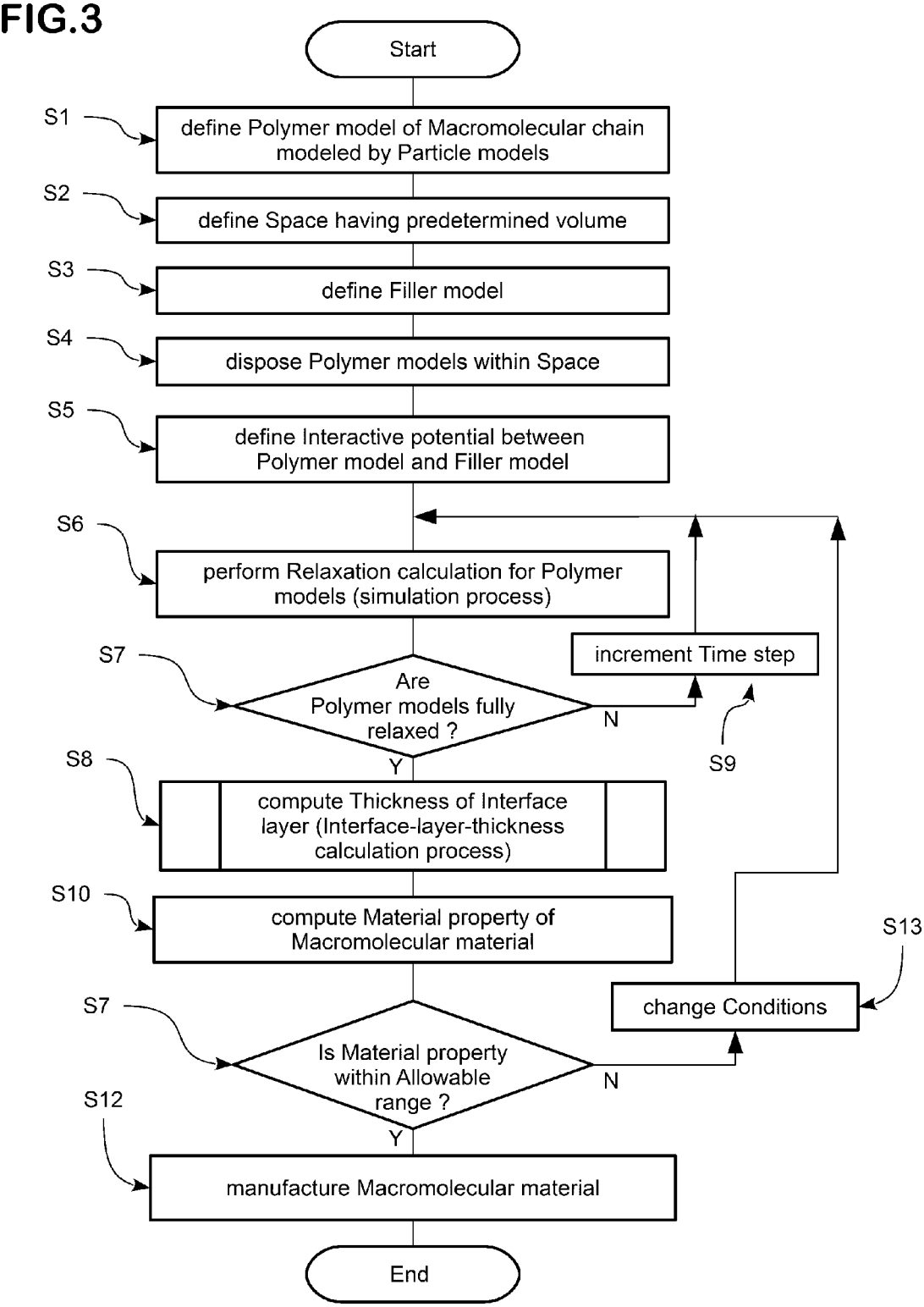
FIG. 3 is a flow chart of a simulation method according to the present invention.

FIG. 3 shows a flowchart of the simulation method common to the following embodiments.

This simulation method comprises processes in which:— a polymer model 2 of the macromolecular chain of the macromolecular material modeled by a plurality of particle models 3 is defined (process S1);

a space 7 having a predetermined volume is defined (process S2);

a filler model 11 of the filler is defined (process S3);

a plurality of the polymer models 2 are disposed in the space 7 (process S4);

an interactive potential between the polymer model 2 and the filler model 11 is defined (process S5);

a relaxation calculation for the polymer models 2 is performed according to a molecular dynamics calculation (simulation process S6);

it is judged whether an initial arrangement of the polymer models 2 has been fully relaxed or not (process S7);

if not yet fully relaxed, the time step is incremented by a unit time (process S9) and the simulation process S6 is repeated;

if fully relaxed, the thickness of an interface layer is computed from results of the simulation process S6 (interface-layer-thickness calculation process S8);

a materials property of the macromolecular material is computed (process S10);

it is judged whether the material property is within an allowable range or not (process S11);

if outside the allowable range, the conditions, parameters and the like of the polymer model 2 and the space 7 are changed (process S13), and then the processes S6 to S11 are repeated; and if within the allowable range, the macromolecular material is manufactured based on data about the polymer models 2 and the space 7 (process S12).

In the first embodiment, the polymer model 2 is a coarse-grained model of the macromolecular chain modeled by a plurality of beads, therefore, the particle model 3 is such bead.

In the second embodiment, the polymer model 2 is an all-atom model of the macromolecular chain modeled by a plurality of atom models, therefore, the particle model 3 is such atom model.

Process S1 in the First Embodiment

Figure 4:
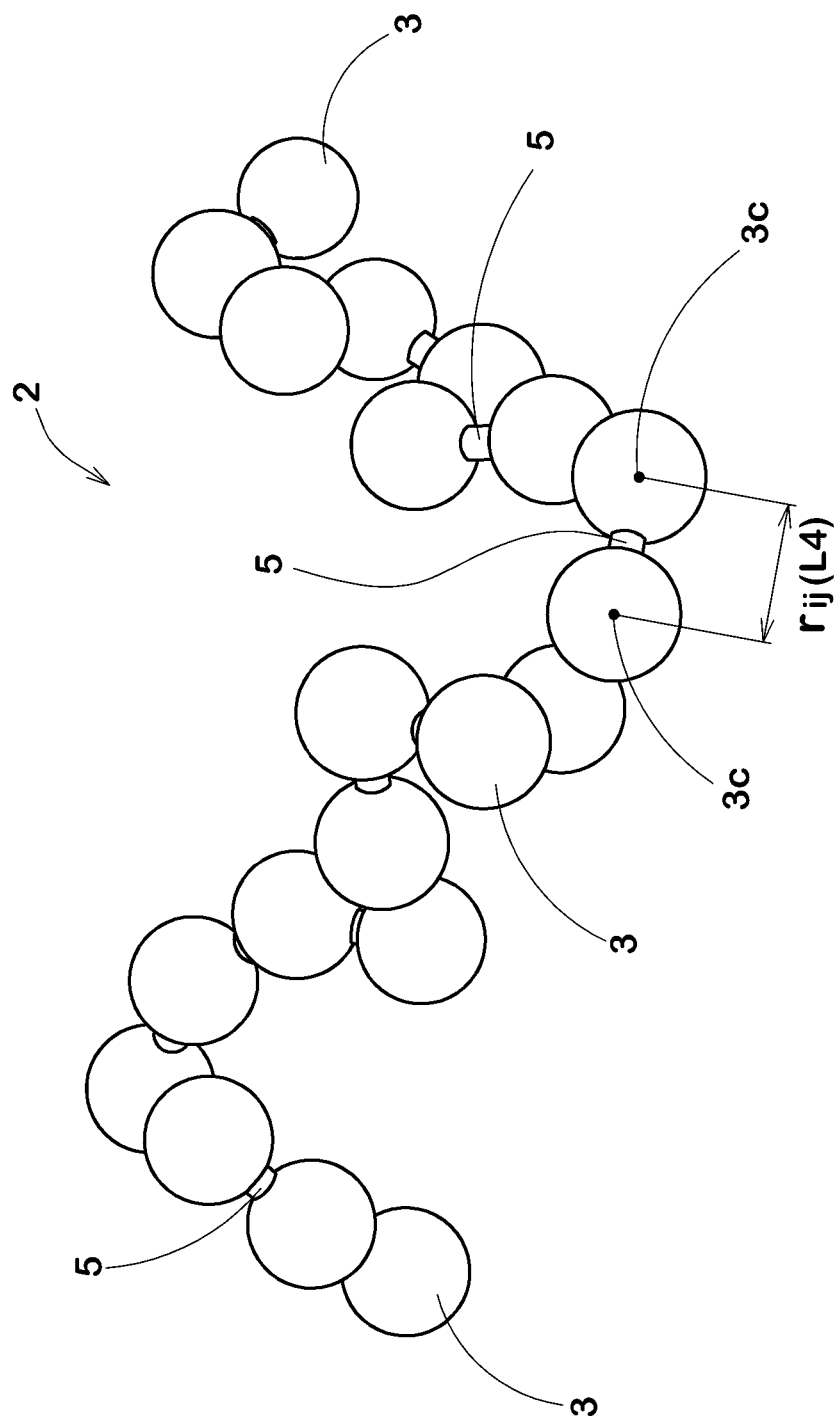
FIG. 4 is a diagram for explaining a coarse-grained model as a polymer model.

In the case of the polybutadiene shown in FIG. 2 and FIG. 4, the macromolecular chain is modeled by beads 3 each corresponding to one structural unit 4 representing 1.55 piece of monomer for example. The reason for 1.55 piece of monomer as one structural unit is based on Non-patent document 1 (L. J. Fetters, D. J. Lohse and R. H. Colby, "Chain Dimension and Entanglement Spacings" Physical Properties of Polymers Handbook second Edition P448), and Non-patent document 2 (Kurt Kremer & Gary S. Grest, "Dynamics of entangled linear polymer melts: A molecular-dynamics simulation" J. Chem Phys. vol. 92, No. 8, 15 Apr. 1990).

In the case that the macromolecular chain is not that of the polybutadiene, the structural unit can be determined based on these non-patent documents too.

In any case, the polymer model 2 of the macromolecular chain modeled by 10 to 5000 particle models (beads) 3 is defined.

In a molecular dynamics calculation, such particle model 3 are treated as mass points in the motion equation.

Therefore, on each of the particle models (beads) 3, parameters such as the mass, volume, electrical charge and initial stage coordinate are defined, and such parameters are stored in the computer 1 as numerical data.

On the polymer model 2, a bond 5 between particle models (beads) 3 is defined.

The bond 5 is defined by a coupling potential P1.

The coupling potential P1 is defined by the sum (R+G) of a potential R and a potential G.

The potential R is given by the following expression (1) and exerts a force including a repulsive force.

In this example, the potential R exerts a repulsive force only. In this application, a potential which exerts a repulsive force only is called "repulsive force potential").

The potential G is an attraction potential G given by the following expression (2).

$$R = \begin{cases} 4\varepsilon\left(\left(\frac{\sigma}{r_{ij}}\right)^{12} - \left(\frac{\sigma}{r_{ij}}\right)^{6} + \frac{1}{4}\right) & \text{if } r_{ij} < 2^{\frac{1}{6}}\sigma \\ 0 & \text{if } r_{ij} \geq 2^{\frac{1}{6}}\sigma \end{cases} \qquad \text{expression (1)}$$

$$G = \begin{cases} -0.5kR_0^2 \ln\left[1 - \left(\frac{r_{ij}}{R_0}\right)^2\right] & \text{if } r_{ij} < R_0 \\ \infty & \text{if } r_{ij} \geq R_0 \end{cases} \qquad \text{expression (2)}$$

wherein
$r_{ij}$ is the distance between two beads,
k is a spring constant between the beads,
$\varepsilon$ is a coefficient relating to the intensity of the repulsive force potential R defined between the beads,
$\sigma$ is a coefficient relating to the distance within which the repulsive force potential R defined between the beads exerts (namely, the diameter of Lennard-Jones sphere known in the field of the molecular dynamics), and
$R_0$ is the full extension length.

These are the parameters of the Lennard-Jones potential.

The distance $r_{ij}$ and the full extension length $R_0$ are those between the centers 3c of the beads 3.

In the above-mentioned expression (1), the shorter the distance $r_{ij}$ between the beads 3, the higher the repulsive force potential R. And the repulsive force potential R increases to infinity as the distance $r_{ij}$ decreases. Such a repulsive force potential R is based on the molecular motion of a macromolecular material.

In the above-mentioned expression (2), the longer the distance $r_{ij}$, the higher the attraction potential G.

Therefore, the coupling potential P1 defines a restoring force to restore the distance $r_{ij}$ to a distance at which the repulsive force potential R and the attraction potential G are balanced with each other.

In the above-mentioned expression (2), if the distance $r_{ij}$ is the full extension length $R_0$ or more, the attraction potential G becomes infinite.

Therefore, the coupling potential P1 does not accept the distance $r_{ij}$ becoming not less than the full extension length $R_0$. Such coupling potential P1 can make the motion of the coarse-grained model 2 approximate the molecular motion of the macromolecular material.

The parameters of the repulsive force potential R and attraction potential G may be arbitrarily determined.

In this example, based on the above-mentioned Non-patent document 2, the parameters are defined as follows.
k: 30
$R_0$: 1.5
$\varepsilon$: 1.0
$\sigma$: 1.0

Instead of the coupling potential P1, a coupling potential P2 given by the following expression (3) can be defined as the bond 5.

$$P2 = \frac{1}{2}k(r - r_0)^2 \qquad \text{expression (3)}$$

wherein
r is the distance between the beads,
$r_0$ is the equilibrium length, and
k is a spring constant between the beads.

Such coupling potential P2 is of a Harmonic type, in which a linear spring is defined between the beads, and thereby it exerts a restoring force whose magnitude is proportional to the difference of the distance r from the equilibrium length $r_0$. Incidentally, the distance r and the equilibrium length r 0 are defined by a distance between the centers of the beads or particle models.

In the above-mentioned expression (3), if the distance r is equal to the equilibrium length $r_0$, the coupling potential P2 becomes zero.

If the distance r is more than the equilibrium length $r_0$, the coupling potential P2 (as attraction potential) increases to infinity as the distance r increases so that the beads 3 approach to each other.

If the distance r is less than the equilibrium length $r_0$, the coupling potential P2 (as repulsive force potential) increases as the distance r decreases so that the beads 3 separate from each other.

Therefore, the coupling potential P2 exerts a restoring force to restore the distance r to the equilibrium length $r_0$.

In the coupling potential P2, differently from the coupling potential P1, the upper limit of the distance r is not limited to the equilibrium length $r_0$. Therefore, the coupling potential P2 accepts the distance r becoming more than the equilibrium length $r_0$. Such coupling potential P2 can prevent a calculation failure during a molecular dynamics calculation due to a large force caused by entangling of the coarse-grained models 2.

The spring constant k and the equilibrium length $r_0$ of the expression (3) may be arbitrarily determined.

In this example, these parameters are defined as follows, based on the above-mentioned Non-patent document 2 similarly to the coupling potential P1.
k: 900
r0: 0.9

Repulsive Force Potential R

Figure 5:
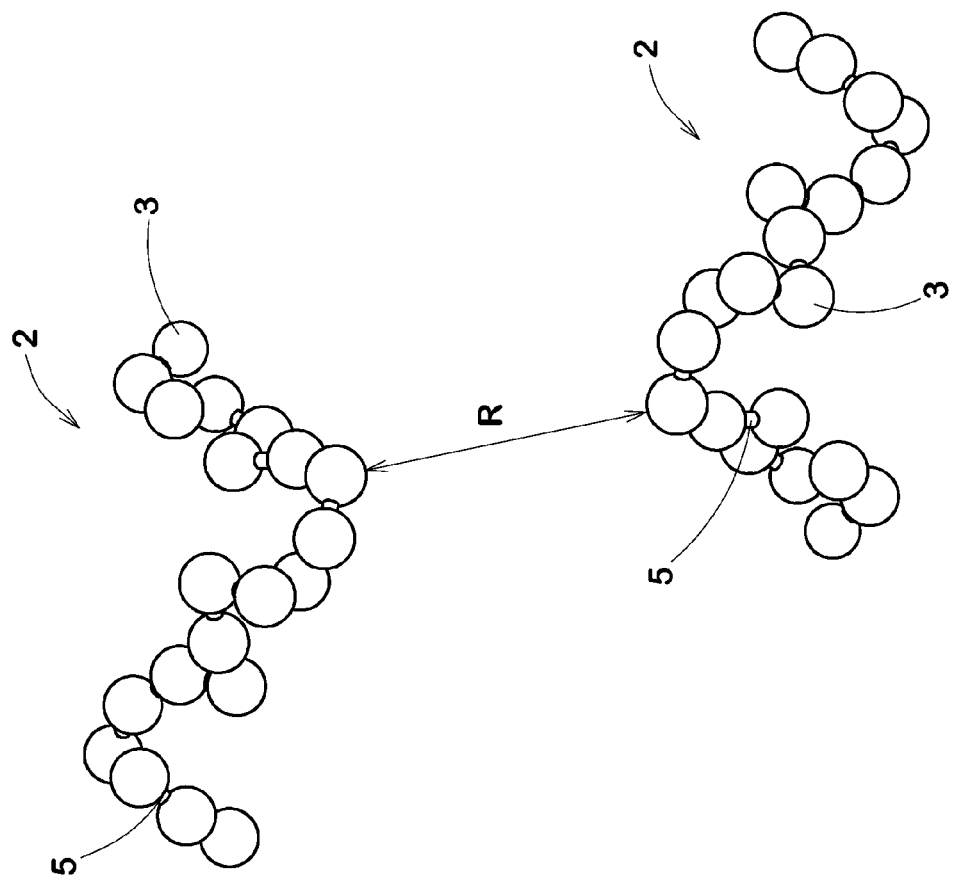
FIG. 5 is a diagram for explaining a potential between coarse-grained models as polymer models.

As shown in FIG. 5, between the polymer models 2, namely, between the particle models 3 of the polymer models 2, the repulsive force potential R given by the above expression (1) is defined. It is desirable that the parameters $\varepsilon$ and $\sigma$ of the repulsive force potential R are set in the same manner as explain above.

Instead of the repulsive force potential R given by the expression (1), the repulsive force potential R given by the following expression (A1) can be defined between the particle models 3 of the polymer models 2.

$$R = \begin{cases} \frac{1}{2}\left[a_{ij}\left(1 - \frac{r_{ij}}{r_c}\right)^2\right] & \text{if } r_{ij} < r_c \\ 0 & \text{if } r_{ij} \geq r_c \end{cases} \qquad \text{expression (A1)}$$

wherein
$r_{ij}$ is the distance between the particle models (beads),
$a_{ij}$ is a coefficient relating to the intensity of the repulsive force between the particle models, and
$r_c$ is a predetermined cutoff distance.

The distance $r_{ij}$ and the cutoff distance $r_c$ are defined by the distance between the centers 3c of the particle models 3.

The above-mentioned expression (A1) is based on the dissipative particle dynamics (DPD) method. The dissipative particle dynamics method is a kind of the coarse grained molecular dynamics method. In the dissipative particle dynamics method, the calculation is made, taking into account a random force and a frictional force depending on the particle velocity, as the forces exerted on the beads in addition to the force due to the interactive potentials. According to such dissipative particle dynamics method, a high-speed simulation of the Brownian movement of molecules is possible.

In the above-mentioned expression (A1), if the distance $r_{ij}$ is equal to or more than the cutoff distance $r_c$, the repulsive force potential R becomes zero.

If the distance $r_{ij}$ is less than the cutoff distance $r_c$, the repulsive force potential R increases as the distance $r_{ij}$ decreases.

Further, even if the distance $r_{ij}$ becomes zero, the repulsive force potential R has a finite value differently from the Lennard-Jones potential increasing to infinity.

Therefore, the repulsive force potential R is prevented from increasing to infinity due to a large force caused by entangling of the polymer models 2, and a calculation failure during a molecular dynamics calculation can be prevented.

Thus, the polymer models 2 can be smoothly relaxed for a short computational time, therefore it becomes possible to simulate a long-time phenomenon.

The parameters of the repulsive force potential R may be arbitrarily determined. In this example, the parameters are defined as follows, based on Non-patent document 3 (Robert D. Groot and Patrick B. Warren "Dissipative particle dynamics: Bridging the gap between atomistic and mesoscopic simulation", J. Chem Phys. vol. 107, No. 11, 15 Sep. 1997).

aij: 25
rc: 1.0

In any case, such polymer model 2 is numerical data which are processable by the computer 1 and stored in the computer 1.

Process S2

Figure 6:
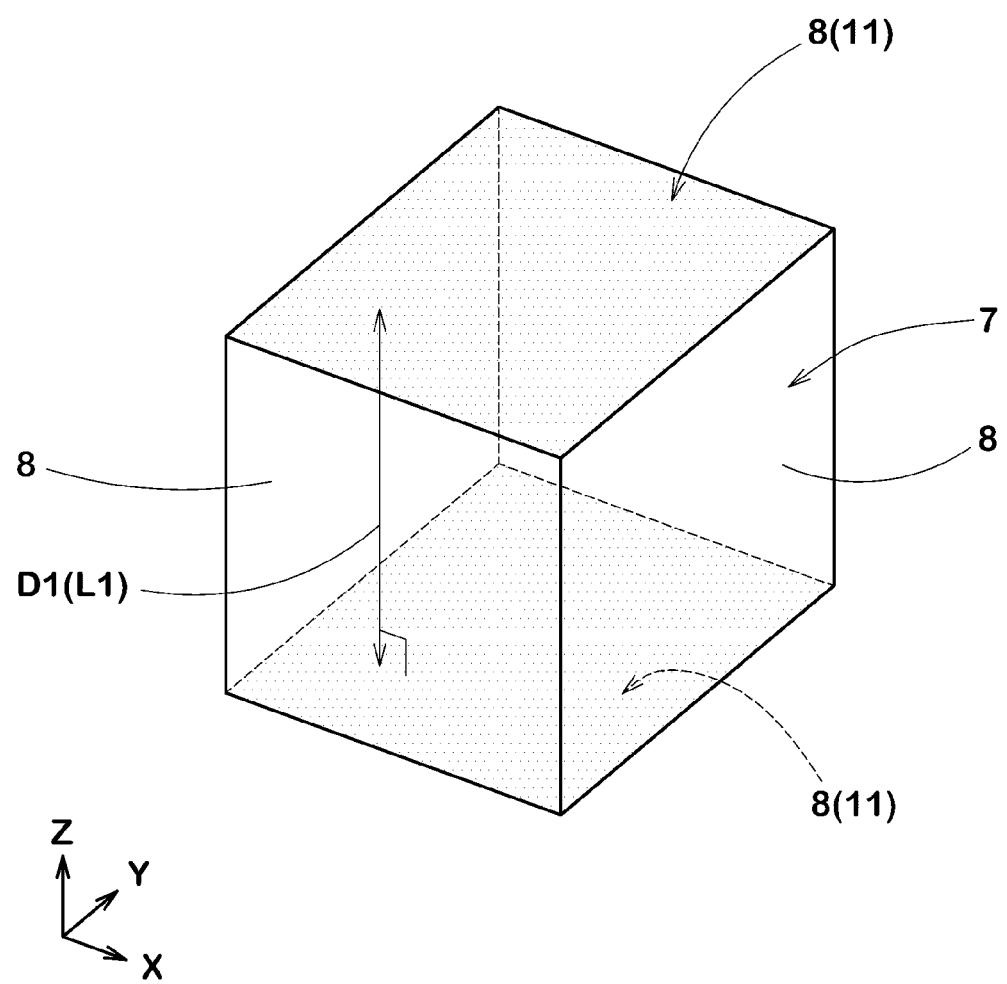
FIG. 6 is a diagram for explaining a space in which the polymer models are disposed and a filler model.

In this process S2, the space having a predetermined volume is defined in the computer 1. The space 7 has a plane forming at least part of its outer surface. In this example, as shown in FIG. 6, the space 7 is defined as a cube having three pairs of oppositely opposed planes 8 forming its entire outer surface.

It is desirable that the distance D1 between the paired planes 8 measured in a direction perpendicular to the planes 8 (accordingly, the length L1 of one side) is set in a range of not less than 2 times, more preferably not less than 4 times the radius of inertia of the polymer model 2 (FIG. 4).

Thereby, during a molecular dynamics calculation, the polymer model 2 can make rotational motions smoothly within the space 7. Incidentally, the radius of inertia is a parameter representing the extension of a polymer model in a molecular dynamics calculation.

The size of the space 7 can be arbitrarily determined so that, for example, the number density of the particle models becomes about 0.85 particle/$\sigma^3$ based on the above-mention non-patent documents 1, 2, or about 3 particle/$\sigma^3$ based on the above-mention non-patent document 3.

In any case, such space 7 is numerical data which are processable by the computer 1 and stored in the computer 1.

Process S3

In this process S3, the filler model of the filler is defined in the computer 1.

Figure 8:
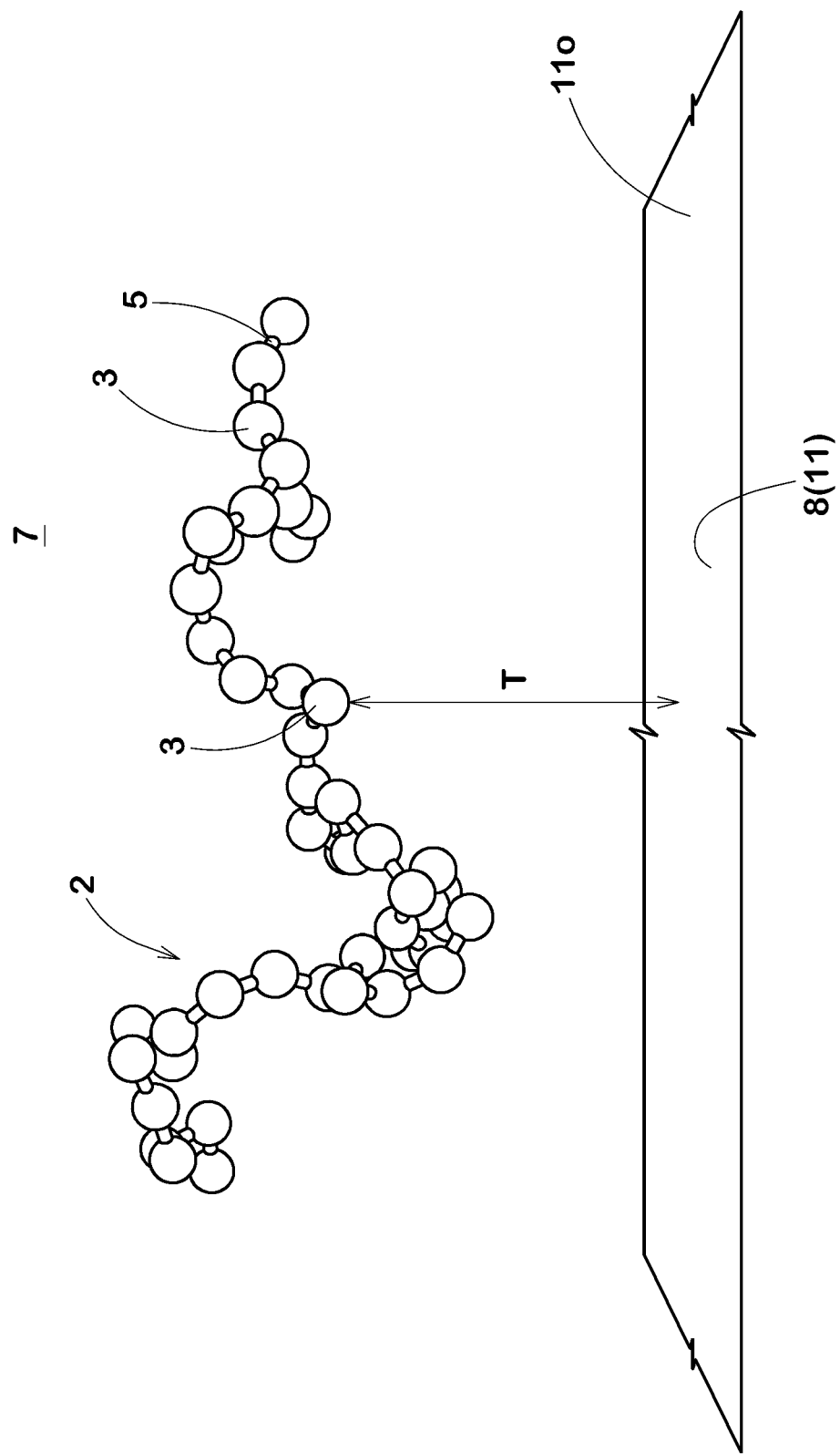
FIG. 8 is a diagram for explaining an interactive potential between a polymer model (coarse-grained model) and a filler model.

In the filler model 11 in this example, a filler particle or aggregation of the filler is modeled by one of the planes 8 of the space 7 (FIG. 8), and in this example, two filler particles are modeled by the upper and lower planes 8 of the space 7. Therefore, a pair of the filler models 11 fixed relatively to the space 7 are defined.

Such filler model 11 can be considered as representing a part of the outer surface 11o of a filler particle of aggregation.

The filler model 11 (outer surface 11o) or the plane 8 of the space 7 is defined as being impossible for the polymer model 2 to pass through.

Such filler models 11 are numerical data which are processable by the computer 1 and stored in the computer 1.

On the remaining planes 8 which do not form the filler model 11, a cyclic boundary condition is defined.

Process S4.

Figure 7:
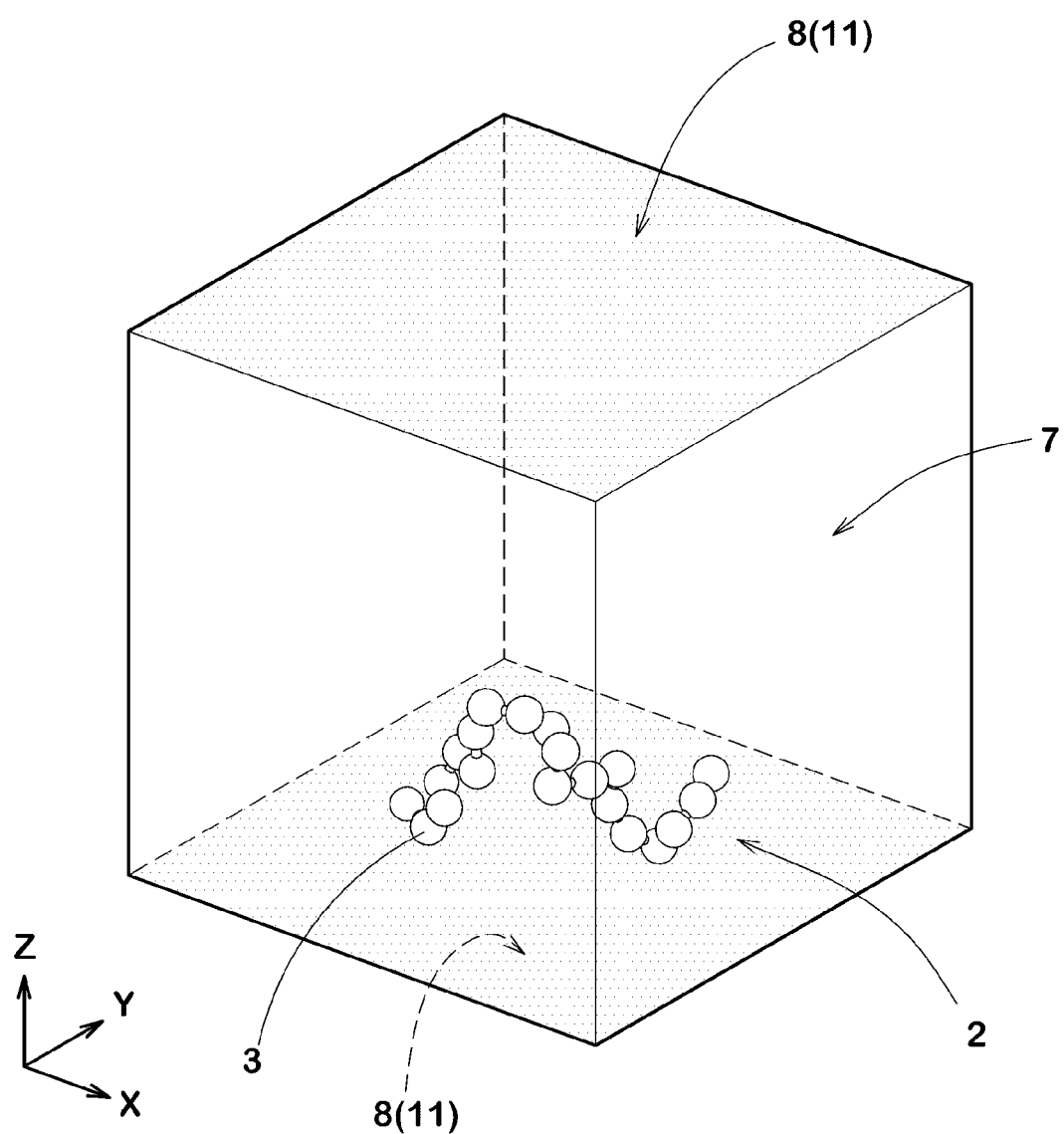
FIG. 7 is a diagram showing the space including the polymer models disposed therein.

In this process S4, as shown in FIG. 7, a plurality of the polymer models 2 are disposed in the space 7. Thereby, the space 7 is constructed as a minute fraction of the macromolecular material as the analysis object. In this example, the polymer models 2 are disposed between a pair of the filler models 11. Preferably, the number of the polymer models 2 is about 200 or more and about 4000 or less for example about 400 or less.

Process S5

In this process S5, the interactive potential T between a particle model of 3 and a filler model 11 is defined in the computer 1.

The interactive potential T is to exert an attractive force or repulsive force. Such interactive potential T is given by the following expression (4).

$$T = \begin{cases} 4\pi\rho_{wall}\varepsilon_{wall}\left[\frac{1}{5}\left(\frac{\sigma_{wall}}{r}\right)^{10} - \frac{1}{2}\left(\frac{\sigma_{wall}}{r}\right)^{4}\right] & \text{if } r < r_c \\ 0 & \text{if } r \geq r_c \end{cases} \quad \text{expression (4)}$$

wherein
r is the distance between the filler model and the particle model,
$r_c$ is the predetermined cutoff distance,
$\rho_{wall}$ is a coefficient relating to the areal density of the interactive potential T,
$\varepsilon_{wall}$ is a coefficient relating to the intensity of the interactive potential T, and
$\sigma_{wall}$ is a coefficient relating to the distance from the filler model (plane 8).

The distance r and the cutoff distance $r_c$ are defined by the shortest distance from the center 3c of the particle model 3 to the plane 8 as the filler model 11.

The interactive potential T given by the above-mentioned expression (4) corresponds to the repulsive force potential R given by the above-mentioned expression (1) which is integrated over the area of the plane 8 as the filler model 11.

Thus, the interactive potential T is defined all over the outer surface 11o as the filler model 11.

In the above-mentioned expression (4), if the distance r is equal to or more than the cutoff distance $r_c$, the interactive potential T becomes zero.

When the distance r is less than $\sigma_{wall} \times 2^{1/6}$, the interactive potential T exerts a repulsive force only between the particle model 3 of the polymer model 2 and the filler model 11.

When the distance r is more than $\sigma_{wall} \times 2^{1/6}$, the interactive potential T can exert an attractive force between the particle model 3 of the polymer model 2 and the filler model 11.

Thus, in the above-mentioned expression (4), between the particle model 3 of the polymer model 2 and the filler model 11, an attractive force or a repulsive force is exerted in the alternative depending on the distance r.

The parameters $\rho_{wall}$, $\sigma_{wall}$, $\epsilon_{wall}$ and $r_c$ of the interactive potential T may be arbitrarily determined.

In this example, these parameters are defined as follows, based on the above-mention Non-patent documents 1, 2.

$\rho_{wall} = \sigma_{wall} = 1.0$
$\epsilon_{wall} = 1$
$r_c = 2^{1/6}$

Simulation Process S6

In this process S6, utilizing the space 7 including the filler models 11 and the polymer models 2, the computer 1 performs a relaxation calculation according to a molecular dynamics calculation.

In the molecular dynamics calculation, the Newton's motion equation is utilized on the premise that the polymer models 2 in the space 7 conform to the classical dynamics for a given length of time. Then, motions of the particle models 3 at each time step are tracked and stored in the computer 1.

During the calculation, the number of the particle models 3, the volume and the temperature in the space 7 are kept at constant values.

In the simulation process S6, since the filler models 11 in this example are positionally fixed to the space 7 as explained above, the relaxation calculation is made on the polymer models 2 only. Therefore, the computational time can be reduced in comparison with the conventional method in which the relaxation calculation is made on both of filler models and polymer models disposed in a space.

Further, the filler model 11 exerts the interactive potential T in the direction perpendicular to the outer surface 11o all over the outer surface 11o. (FIG. 8) In other words, the interactive potential T which the filler model 11 exerts on the polymer models 2 is in one direction all over the plane 8, therefore, the relaxation calculation for the polymer models 2 can be made simply and effectively.

In this example, since the repulsive force potential which increases to infinity as the distance $r_{ij}$ between the particle models 3 decreases, is defined between the particle models 3 of the polymer model 2, it is possible to accurately relax the initial arrangement of the polymer models 2 so as to approximate actual molecular motions of the macromolecular material.

Process S7

In this process S7, the computer 1 judges if the initial arrangement of the polymer models 2 has been fully relaxed.

If not yet fully relaxed, the time step is incremented by a unit time. (process S9)

Then, the simulation process S6 (molecular dynamics calculation) is repeated.

If fully relaxed, the process goes to the next interface-layer-thickness calculation process S8.

Figure 9:
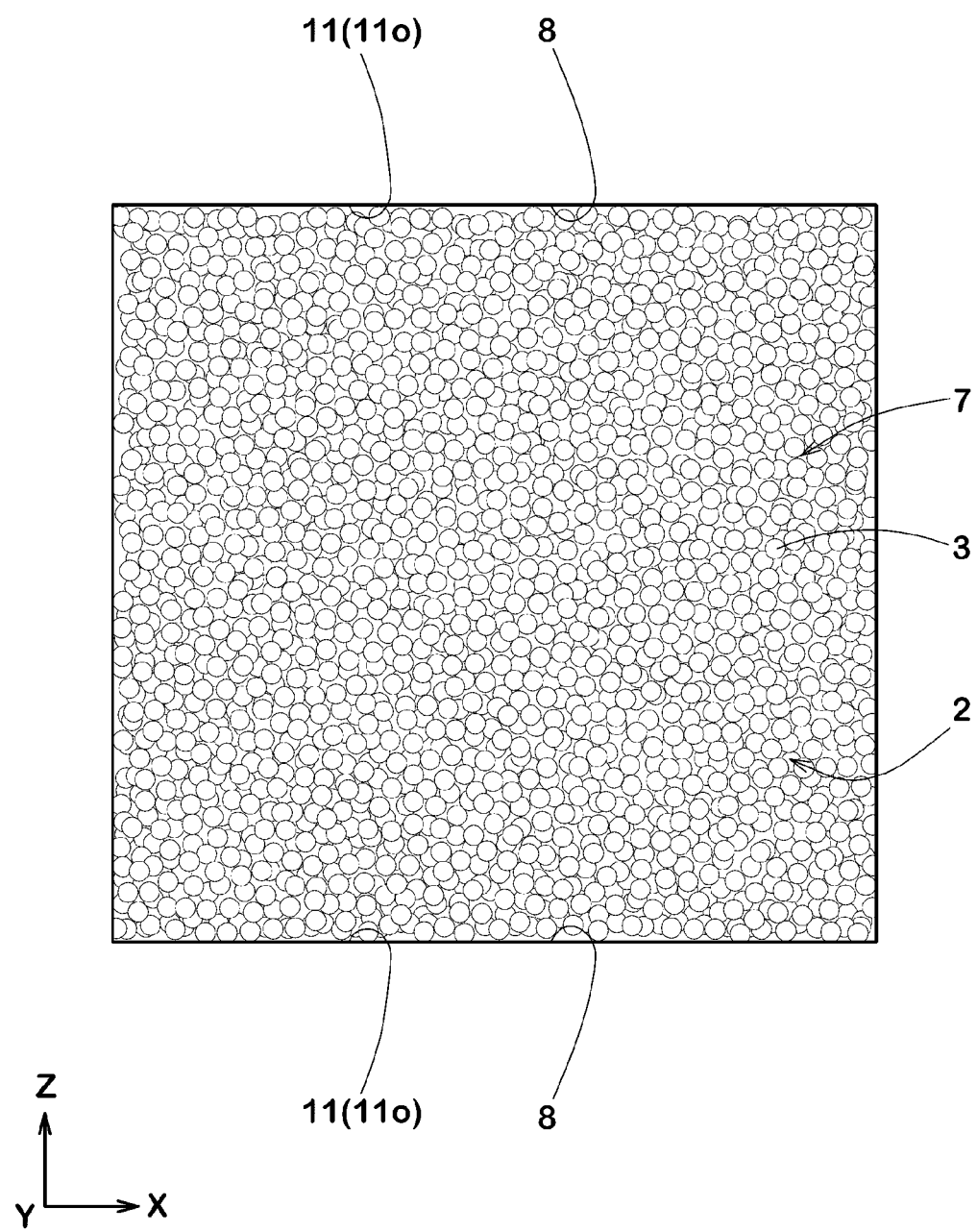
FIG. 9 is a diagram showing an equilibrium state of the coarse-grained models as the polymer models in the space.

In the simulation process S6, therefore, an equilibrium state (structurally relaxed state) of the polymer models 2 as showsn in FIG. 9, can be computed certainly.

Interface-Layer-Thickness Calculation Process S8

In this process S8, from the results of the simulation process S6, the thickness of the interface layer of the macromolecular material is computed by the computer 1.

Figure 10:
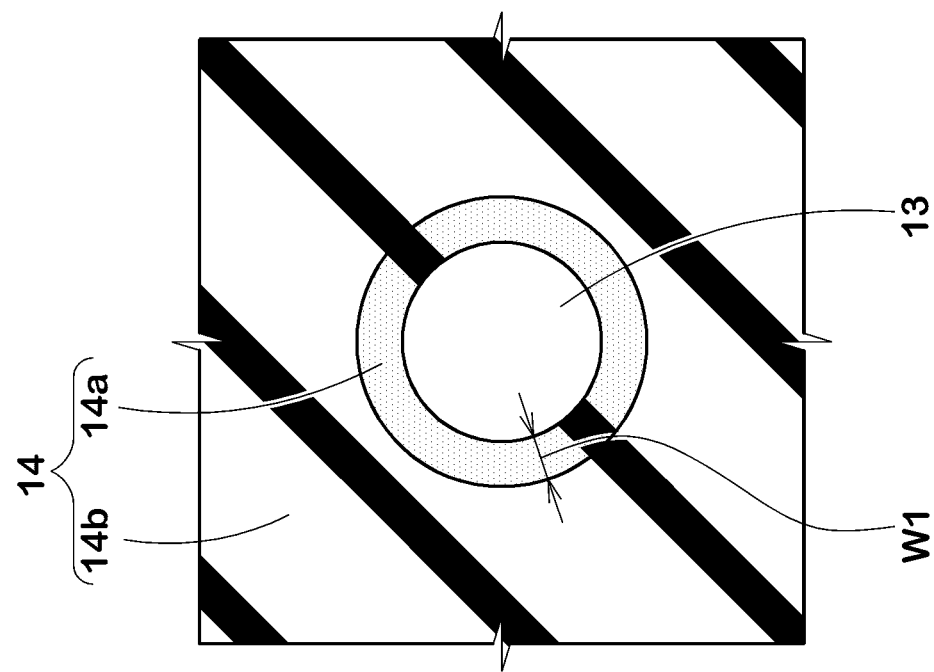
FIG. 10 is a schematic cross sectional view for explaining an interface layer formed around a filler particle mixed in a macromolecular material.

In a system in which the filler and the macromolecular material 14 exist together, as shown in FIG. 10, the interface layer 14a having a different dynamic property than the bulk 14b namely the macromolecular material 14 itself, is formed around the filler particle 13.

Therefore, it is important that the thickness w1 of the interface layer 14a is defined before the material property of the macromolecular material is computed by the use of the space 7 (FIG. 9) constituted as a minute fraction of the macromolecular material.

Figure 11:
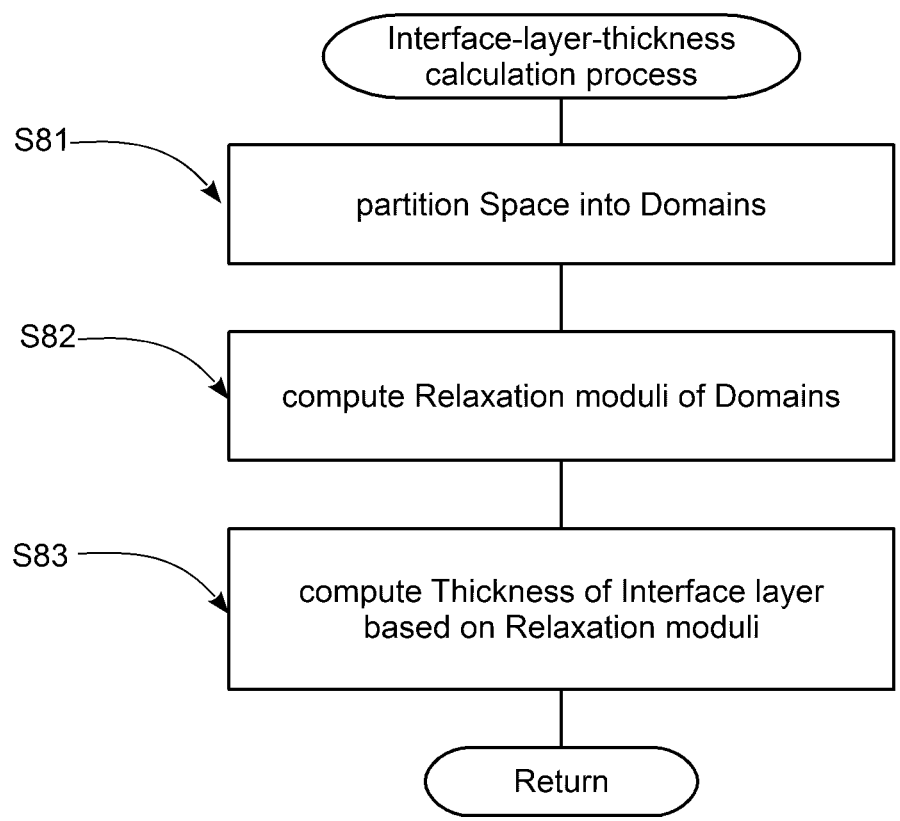
FIG. 11 is a flow chart of an interface-layer-thickness calculation process for computing the thickness of the interface layer according to the present invention.

FIG. 11 shows a flowchart of the interface-layer-thickness calculation process S8 in this example.

Process S81

In this process S81, the computer 1 partitions the space 7 in which the polymer models 2 are disposed, into a plurality of domains.

Figure 12:
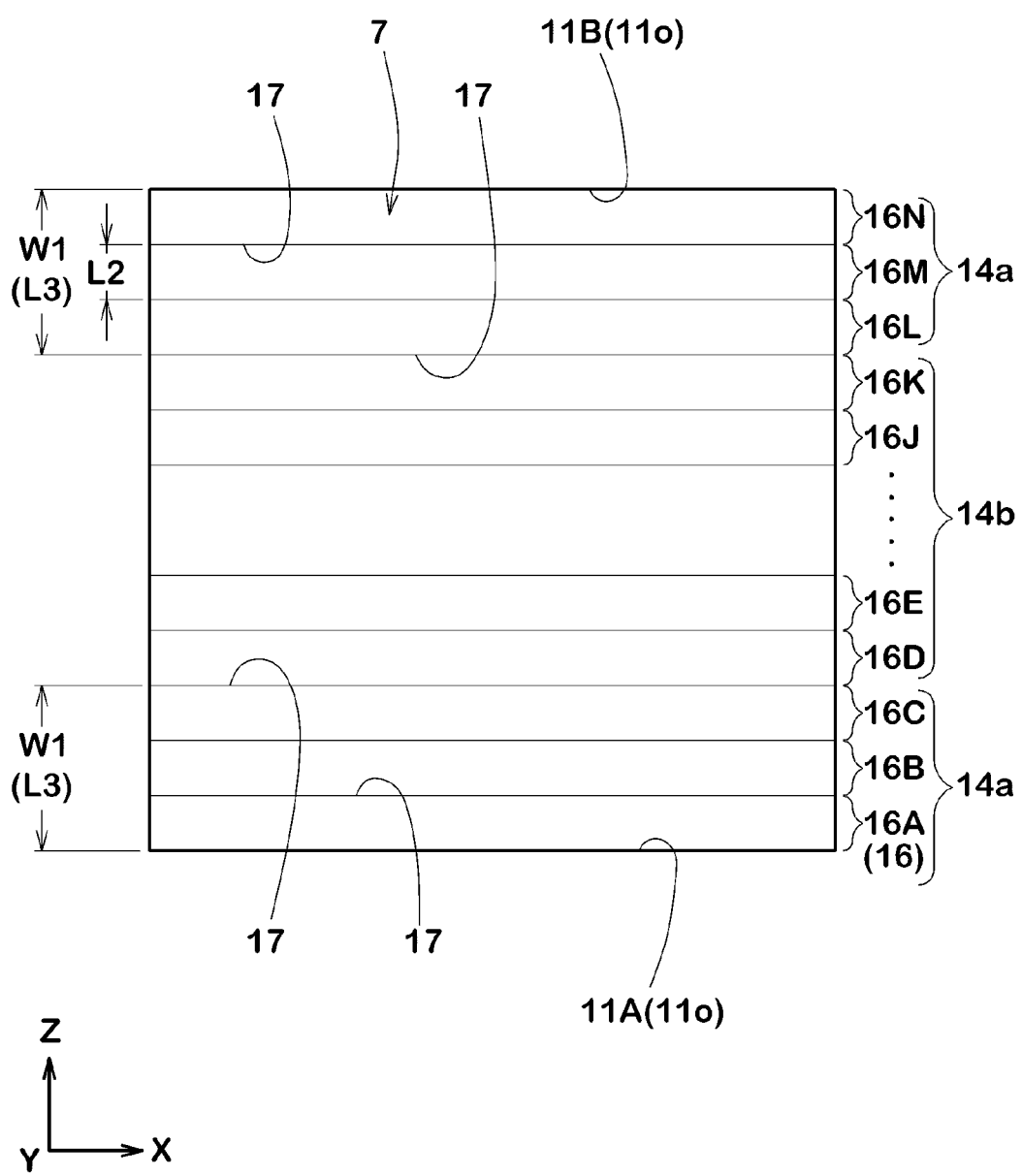
FIG. 12 is a diagram for explaining the interface-layer-thickness calculation process.

As shown in FIG. 12, the space 7 (the polymer models 2 are omitted) is partitioned in the direction from the filler model 11A to the filler model 11B, and the domains 16 are bounded by a plural number (N−1) of boundary surfaces 17 which are parallel with the outer surfaces 11o as the filler models 11A and 11B.

Thereby, in the space 7, there are defined a number N of domains 16 (the first domain 16A on the filler model 11A side to the last Nth domain 16N on the filler model 11B side).

The distances L2 between the boundary surfaces 17 measured perpendicularly to the boundary surfaces 17 are constant, and all the domains 16A to 16N have an identical volume.

Incidentally, such domains 16A to 16N are numerical data stored in the computer 1.

It is desirable that the distances L2 between the boundary surfaces 17 are determined based on the radius of inertia of the polymer model 2 because it is supposed that the interface layer 14a changes depending on the chain lengths of the polymer model 2. For example, the distances L2are set to be the same as the radius of inertia of the polymer model 2.

Relaxation Modulus Calculation Process Sf82

In this process S82, the computer 1 computes the relaxation modulus of each of the domains 16A to 16N.

The relaxation modulus G(t) gives an indication of the change in the elastic modulus of the viscoelastic body in a given time span t when a strain is applied thereto.

The relaxation modulus G(t) of each domain 16A-16N can be obtained by the following expression (5).

$$G(t) = \frac{V}{k_B T} \langle \sigma_{xy}(t+\tau) \times \sigma_{xy}(\tau) \rangle \qquad \text{expression (5)}$$

wherein
V is the volume of the domain,
$k_B$ is the Boltzmann's constant,
T is the absolute temperature,
$\sigma_{xy}$ is the stress in a given orthogonal system xy,
$\tau$ is time, and
t is a time span.

In the above-mentioned expression (5), $\langle \sigma_{xy}(t+\tau) \times \sigma_{xy}(\tau) \rangle$ is the ensemble average of the product of the stress $\sigma_{xy}$ at the time $\tau$ and the stress $\sigma_{xy}$ at the time $(t+\tau)$ which is averaged over the time $\tau$ for a given time period t. Preferably, the computing time for the relaxation modulus G(t) is 1,000$\tau'$ to 10,000,000$\tau'$, wherein 1$\tau'$ is the unit time employed in the simulation.

For each of the domains 16A to 16N, the relaxation modulus G(t) is computed and stored in the computer 1.

As another example of the relaxation modulus calculation process S82, it is possible to compute the relaxation modulus G(t) for every two domains 16 together which two domains are at the same distances from the respective filler models 11A and 11B. As a more concrete example, the relaxation modulus G(t) is computed for the first domain 16A and the last Nth domain 16N together. Therefore, the number of the domains 16 to be computed for the relaxation modulus G(t) becomes substantially one half of the number of all the domains 16A to 16N, and the computational time can be remarkably reduced. Further, the relaxation moduli G(t) are ensemble averaged targeting at double polymer models 2, therefore, it is possible to compute the relaxation modulus G(t) with accuracy.

In this case, it is desirable to compute the relaxation modulus G(t) by multiplying the z axis component of the stress σxy by "−1" with respect to one of the two domains 16, for example, one of the first domain 16A and the Nth domain 16N, because, the directions of the stress σxy on the z axis of the two domains become opposite directions.

Determining Process S83

In this process S83, based on the obtained relaxation moduli of the domains 16A to 16N, the thickness W1 of the interface layer 14a is computed by the computer 1.

The interface layer 14a shows dynamic properties (including, relaxation modulus G(t)) different than the bulk 14b. Therefore, the computer checks whether or not the difference in the relaxation modulus G(t) between every two of the adjacent domains 16 is within the predetermined range, and decides that the domains 16 of which difference is within the predetermined range are the bulk 14b, and the rest are the interface layer 14a.

Figure 13:
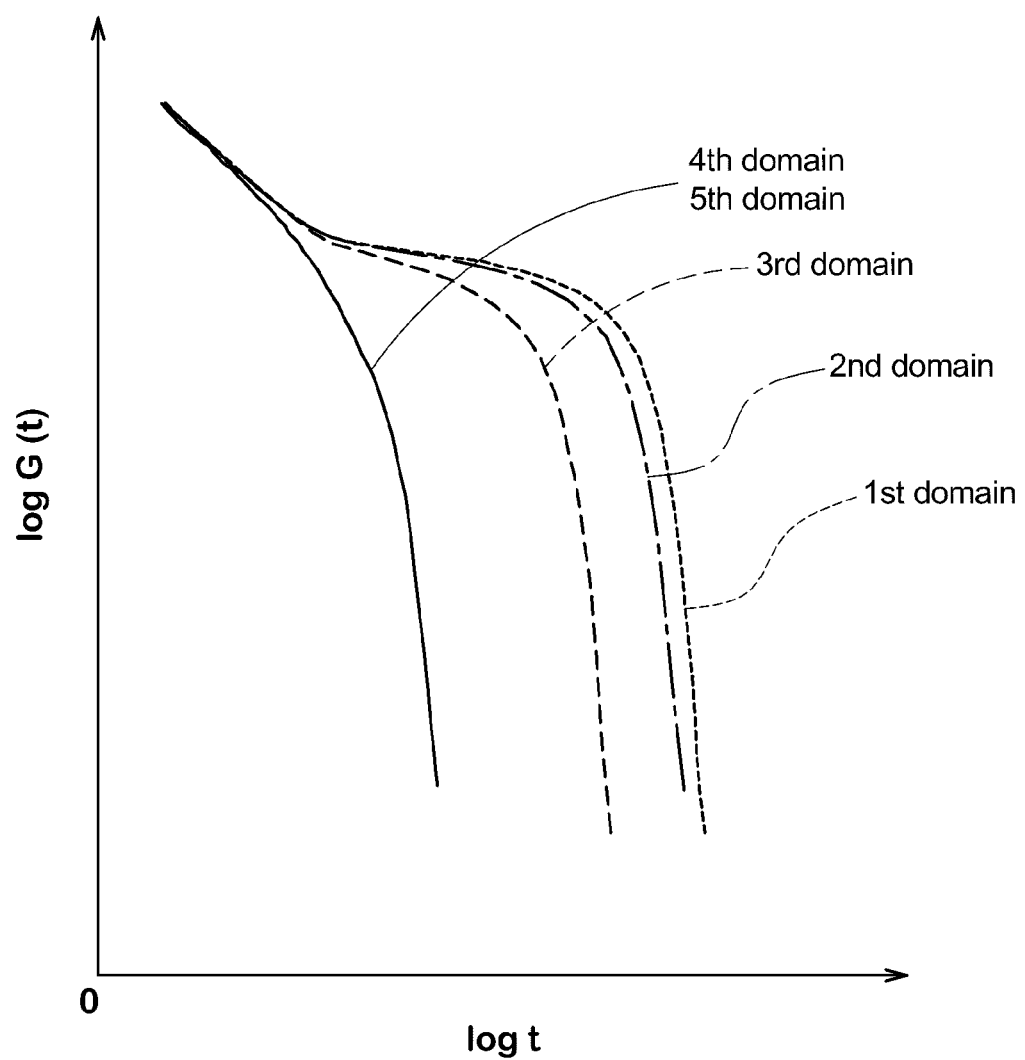
FIG. 13 is a graph showing the relaxation moduli G(t) of first to fifth domains.

FIG. 13 shows, a relation between the natural logarithm of each of the relaxation moduli G(t) of the first-fifth domains 16A-16E counted from one of the filler models (11A), and the natural logarithm of the time span t.

Form this graph, it can be seen that, when compared with the first-third domains 16A-16C, the relaxation modulus G(t) of the fourth domain 16D is the substantially same as that of the fifth domain 16E, therefore, the fourth domain 16D and subsequent domains 16E—as shown in FIG. 12 are determined as the bulk 14b. The first-third domains 16A-16C are determined as the interface layer 14a. Thus, starting from the filler model 11A, the interface layer 14a is determined.

Further, staring from the other filler model 11B, the interface layer 14a on the filler model 11B side is determined in the same manner as above.

Therefore, the interface layers 14a and the bulk 14b therebetween are determined.

For example, if the ratio of two values of natural logarithm of the relaxation moduli G(t) of two adjacent domains is within a range of from 0.7 to 1.3, then it can be decided that the difference in the relaxation modulus G(t) is within a predetermined range as explained above.

Then, the shortest distance L3 between the boundary surface 17 between the interface layer 14a and the bulk 14b (in the example shown in FIG. 12, between the third domain 16C and the fourth domain 16D) and the filler model 11 is computed as the thickness w1 of the interface layer 14a. The obtained thickness w1 is stored in the computer 1.

Therefore, according to the present invention, the thickness of the interface layer can be obtained without the need for the experiment and measurement using the actual macromolecular material and filler as in the conventional simulation method. Further, even if the macromolecular material does not exist yet in reality or is not readily available, the thickness of the interface layer can be obtained. Therefore, it is very helpful to design or develop macromolecular materials.

Process S84

In the interface-layer-thickness calculation process S8, it is desirable that, prior to the relaxation modulus calculation process S82, the computer 1 sets identical values to the distances L4 (FIG. 4) between the adjacent particle models 3 of each of the polymer models 2 in order to reduce the variation of the bond 5 and stabilize the computation of the relaxation modulus G(t). (Process S84)

In this case, it is desirable that the identical values are the same as the value of the equilibrium length of the coupling potential P1 or P2 employed. Thereby, the force between the particle models 3 due to the potential P1 or P2 becomes zero, and the stabilized computation is further facilitated.

Process S10

In this process S10, the computer computes a materials property (for example, complex elastic modulus) of the macromolecular material by defining parameters including the obtained thickness W1 of the interface layer 14a on the space 7 including the polymer models 2, Process S11

In this process S11, the computer 1 judges if the obtained material property of the macromolecular material is within an allowable range.

If outside the allowable range, the conditions set on the space 7 including the coarse-grained models 2 are changed. (process S13)

Then, the processes S6 to S11 are repeated.

If within the allowable range, based on the conditions set on the space 7 including the polymer models 2, the macromolecular material is actually manufactured. (Process S12)

In the simulation method in this example, the conditions set on the space 7 including the polymer models 2 are changed until the materials property of the macromolecular material becomes within the allowable range, therefore, it is possible to effectively design or develop the macromolecular material having desired performance.

Figure 14:
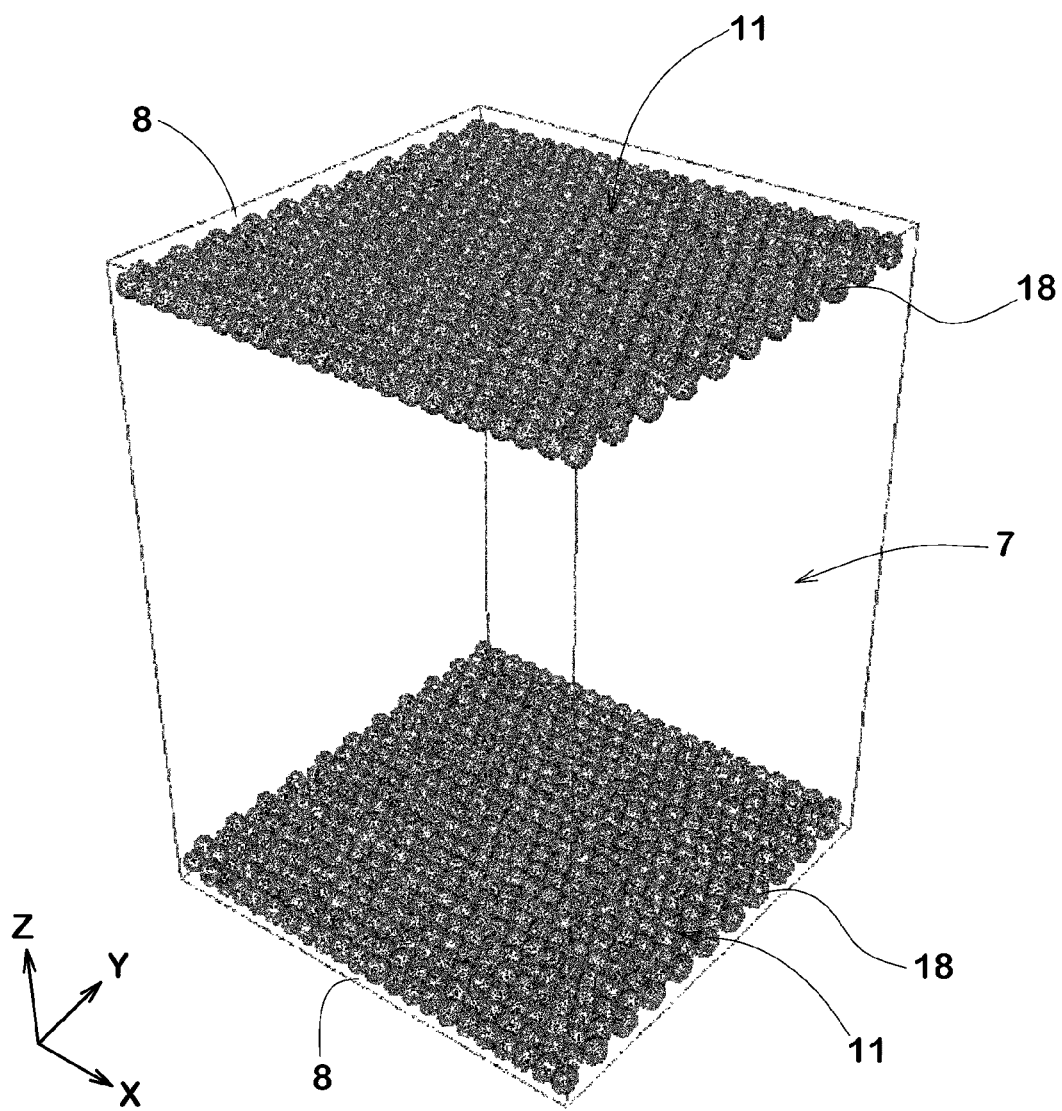
FIG. 14 is a diagram for explaining another example of the filler model.
Figure 15:
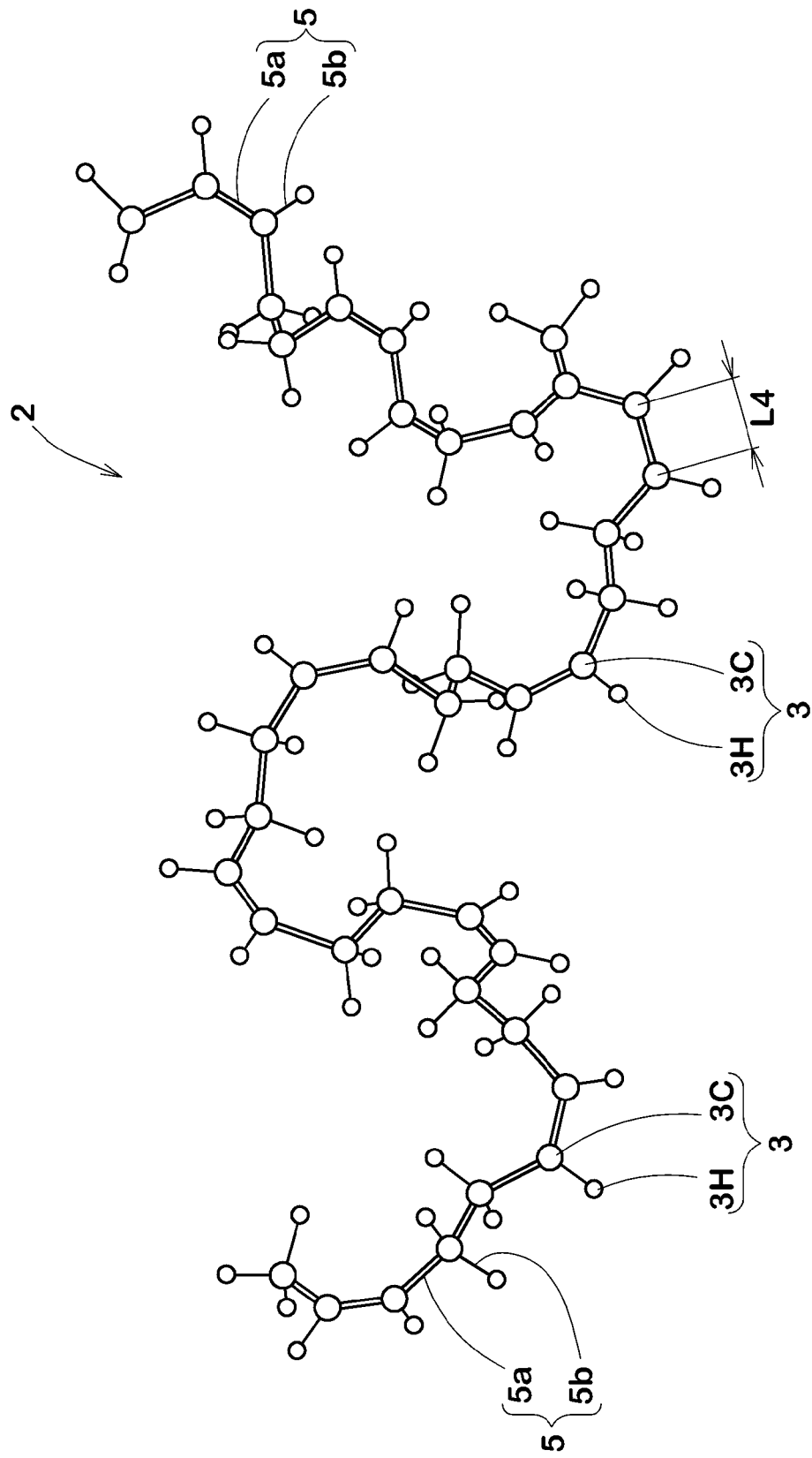
FIG. 15 is a diagram for explaining an all-atom model as a polymer model.

As above described, the filler model 11 is defined by the plane 8 of the space 7. But, it is not limited to this example. For example, as shown in FIG. 14, the filler model 11 can be defined by a plurality of particles 18 disposed along the plane 8 of the space 7. In this case, it is desirable that the repulsive force potential R is defined as the interactive potential between a particle 18 of the filler model 11 and a particle model 3 of the polymer model 2.

Process S1 in the Second Embodiment

As noted above, in the second embodiment, the polymer model 2 is an all-atom model. In this case the process S1 is as follows.

In the all-atom model, all atoms of the macromolecular chain are modeled by atom models. Thus, the particle model 3 is such atom model.

The particle models 3 or atom models in this example include a carbon model 3C of a carbon atom in the macromolecular chain, and a hydrogen model 3H of a hydrogen atom in the macromolecular chain.

In a simulation according to a molecular dynamics calculation, the atom models 3 or particle models are treated as mass points in the motion equation. Namely, on each of the particle models 3, parameters such as the mass, diameter, electrical charge and initial stage coordinate are defined, and the parameters are stored in the computer 1 as numerical data.

A joining chain 5 binding two particle models 3 each other is defined between the particle models 3 in the polymer model 2. In this example, the joining chain 5 includes a main chain 5a binding two carbon models 3c, and a side chain 5b binding a carbon model 3C and a hydrogen model 3H.

Figure 16A:
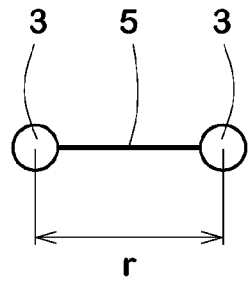
FIGS. 16(a), 16(b) and 16(c) are diagrams for explaining a bond length r, a bond angle θ and a dihedral angle φ.
Figure 16B:
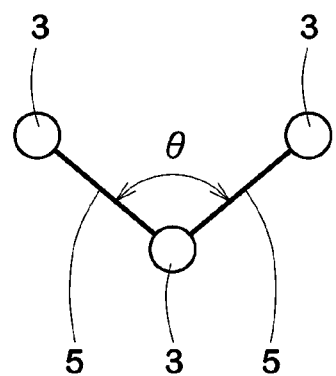
Figure 16C:
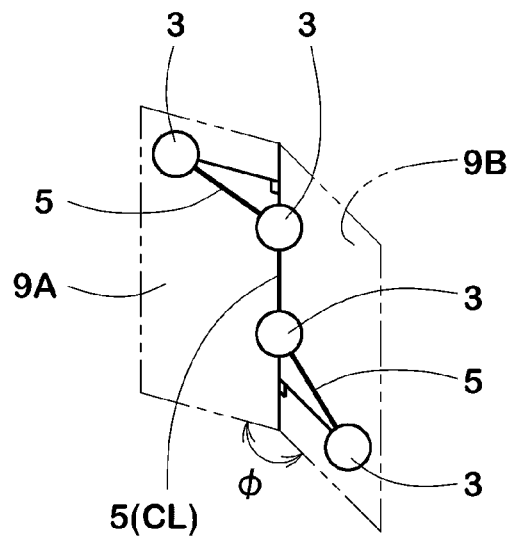

Further, on the polymer model 2, there are defined a bond length r between two particle models 3 as shown in FIG. 16(*a*),
a bond angle θ formed by three particle models 3 which are successive through the joining chains 5 as shown in FIG. 16(*b*), and
a dihedral angle φ formed between a plane 9A formed by one set of three successive particle models 12 of four successive particle models 12 which are successive through the joining chains 5 and a plane 9B formed by the other set of three successive particle models 12 as shown in FIG. 16(*c*).

The bond length r, the bond angle θ and the dihedral angle φ may be changed when an external force or internal force is applied to the polymer model 2.

The bond length r is defined by a coupling potential $U_{bond}(r)$ given by the following expression (B1).

The bond angle θ is defined by a bond angle potential $U_{Angle}(\theta)$ given by the following expression (B2).

The dihedral angle φ is defined by a dihedral angle potential $U_{torsion}(\phi)$ given by the following expression (B3).

$$U_{bond}(r) = \frac{1}{2}k_1(r-r_0)^2 \quad \text{expression (B1)}$$

$$U_{Angle}(\theta) = \frac{1}{2}k_1(\theta-\theta_0)^2 \quad \text{expression (B2)}$$

$$U_{torsion}(\phi) = k_2 \sum_{n=0}^{N-1} A_n \cos^n \phi \quad \text{expression (B3)}$$

wherein
r is the bond length between two particle models,
$r_0$ is the equilibrium length,
$k_1$ is a spring constant between the particle models,
θ is the bond angle,
$\theta_0$ is the equilibrium bond angle,
$k_2$ is a coefficient relating to the intensity of the dihedral angle potential,
N−1 is the degree of a polynomial of the dihedral angle potential,
φ is the dihedral angle,
$A_n$ is a dihedral angle constant.

Incidentally, the bond length r and the equilibrium length $r_0$ are defined as a distance between the centers of the particle models 3.

The coupling potential $U_{bond}(r)$ is a potential of a harmonic oscillator.

A monomer of the polybutadiene is —[CH2-CH=CH—CH2]-.

In this case, the coupling potential $U_{bond}(r)$ is defined on each of CH=CH, CH2-CH2, C—H, and CH—CH2.

The parameters of the coupling potential $U_{bond}(r)$ may be arbitrarily determined. In this example, based on Non-patent document 4 (J. Phys. Chem. 94, 8897 (1990)), the parameters are defined as follows.
CH=CH:
 $k_1$=1400 kcal/mol·Å$^2$
 $r_o$=1.33 Å
CH2-CH2:
 $k_1$=700 kcal/mol·Å$^2$
 $r_0$=1.53 Å
CH3-H:
 $k_1$=700 kcal/mol·Å$^2$
 $r_0$=1.09 Å
CH2-H:
 $k_1$=700 kcal/mol·Å$^2$
 $r_0$=0.99 (Å)
CH—CH2:
 $k_1$=700 kcal/mol·Å$^2$
 $r_0$=1.43 Å

The bond angle potential $U_{Angle}(\theta)$ is also of the harmonic oscillator.

In the above-mentioned case, the bond angle potential $U_{Angle}(\theta)$ is defined on each of CH2-CH2-CH and CH=CH—CH2.

The parameters of the bond angle potential $U_{Angle}(\theta)$ may be arbitrarily determined. In this example, based on the Non-patent document 4, the parameters are defined as follows.
CH2-CH2-CH:
 $k_1$=100 kcal/mol·rad$^2$
 $\theta_0$=109.5 degrees
CH=CH—CH2:
 $k_1$=100 kcal/mol·rad$^2$
 $\theta_0$=120 degrees The dihedral angle potential $U_{torsion}(\phi)$ is a potential relating to a torsion of the molecular chain about an axis CL which is one of the joining chains 5 as shown in FIG. 16(*c*). For example, the dihedral angle potential $U_{torsion}(\phi)$ is defined on each of CH=CH and CH2-CH2.

The parameters of the dihedral angle potential $U_{torsion}(\phi)$ may be arbitrarily determined. In this example, based on non-patent document 4 (J. Phys. Chem. 94, 8897 (1990)), the parameters are defined as follows.
CH2-CH2:
 $k_2$=0.111 kcal/mol
 N=4
 $A_0$=1
 $A_1$=3
 $A_2$=0
 $A_3$=−4

Figure 17:
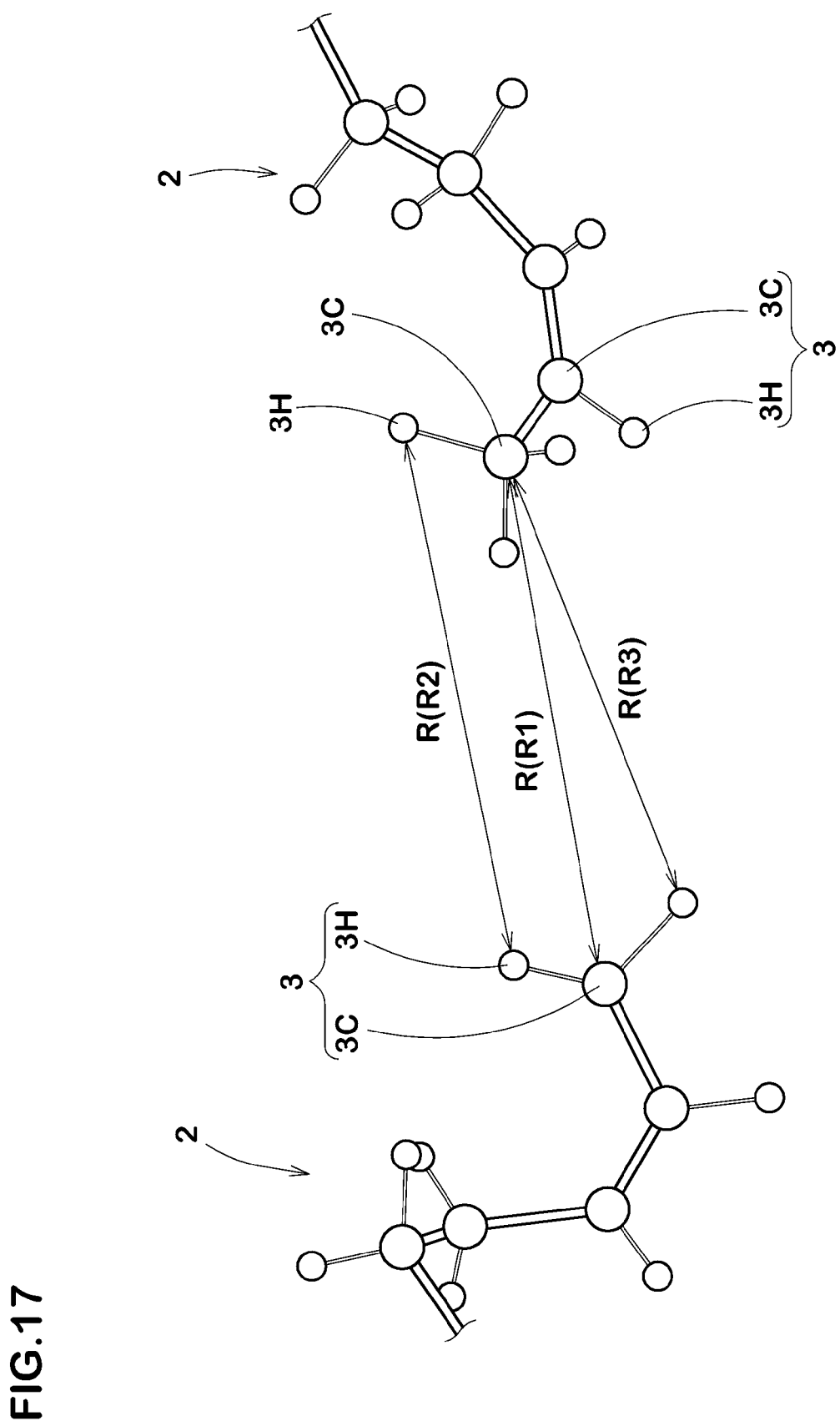
FIG. 17 is a diagram for explaining potentials between all-atom models as the polymer models.
Figure 18:
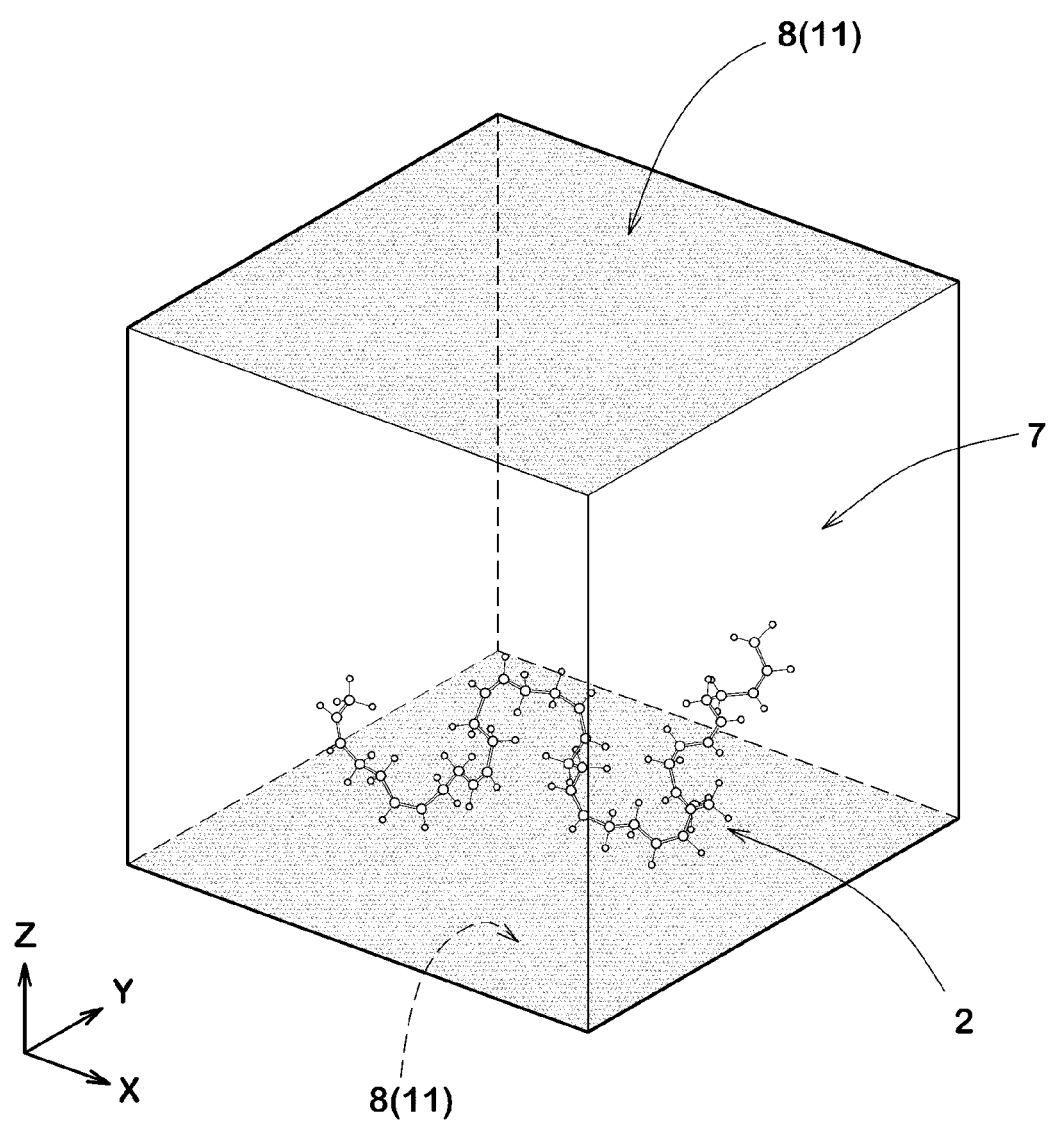
FIG. 18 is a diagram showing the space in which all-atom models are disposed and the filler models.
Figure 19:
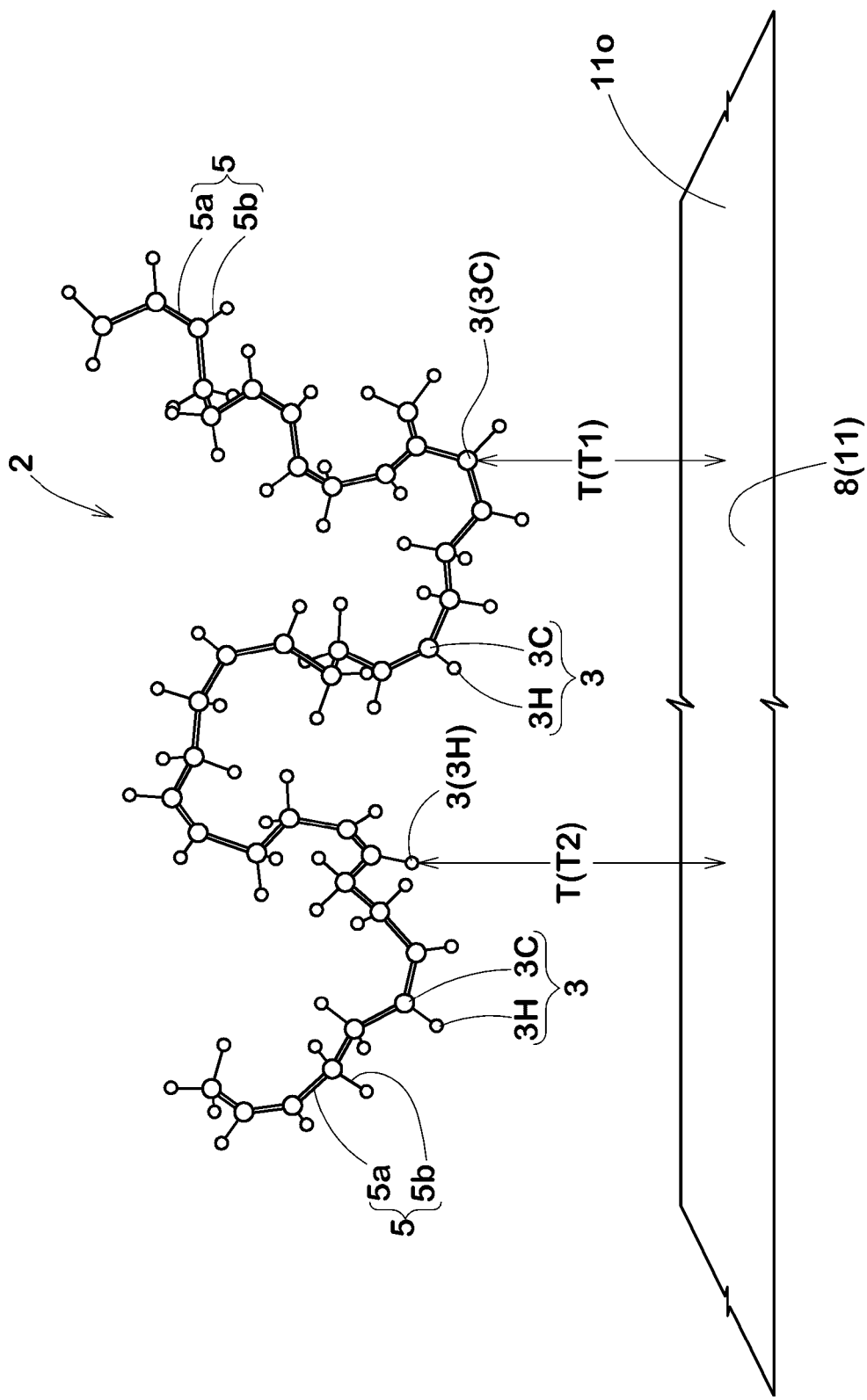
FIG. 19 is a diagram for explaining interactive potentials between a filler model and an all-atom model as a polymer model.
Figure 20:
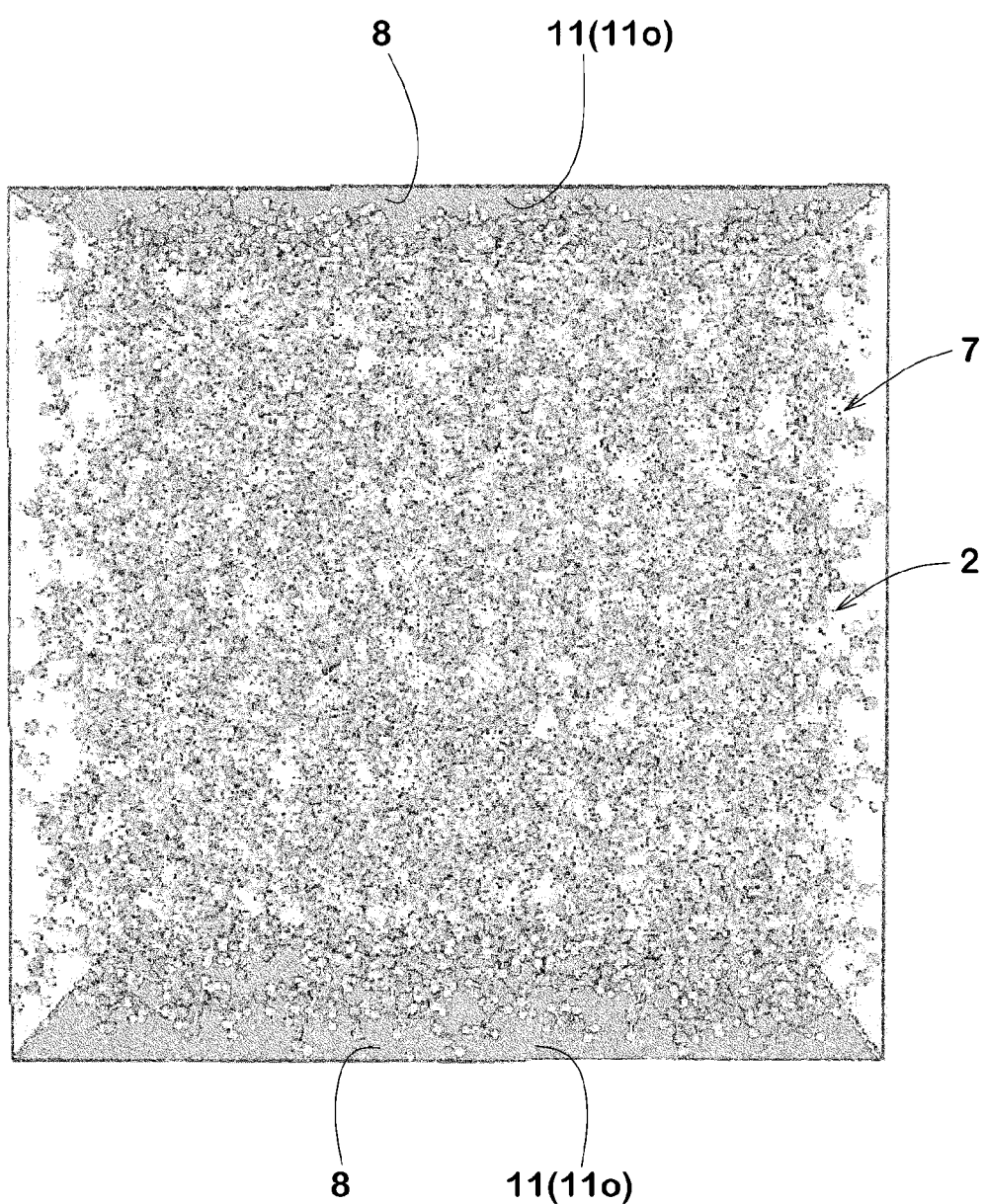
FIG. 20 is a diagram showing an equilibrium state of the all-atom models in the space.

As shown in FIG. 17, between a particle model 3 of a polymer model 2 and a particle model 3 of another polymer model 2, a potential R given by the following expression (B4) is defined.

$$R = \begin{cases} 4\epsilon\left[\left(\frac{\sigma}{r_{ij}}\right)^{12} - \left(\frac{\sigma}{r_{ij}}\right)^6\right] & \text{if } r_{ij} < r_c \\ 0 & \text{if } r_{ij} \geq r_c \end{cases} \quad \text{expression (B4)}$$

wherein
$r_{ij}$ is the distance between two particle models concerned,
ε is a coefficient relating to the intensity of the potential R,
σ is a coefficient relating to the distance within which the potential R defined between the particle models exerts (namely, the diameter of Lennard-Jones sphere known in the field of the molecular dynamics), and
$r_c$ is a cutoff distance.

These are the parameters of the Lennard-Jones potential.
The distance $r_{ij}$ and cutoff distance $r_c$ are defined by the distance between the centers of the particle models 3.

In this example, the potential R between two particle models 3 include a first potential R1 between two carbon models 3*c*, a second potential R2 between two hydrogen models 3H, and a third potential R3 between a carbon model 3*c* and a hydrogen model 3H. The parameters of the above-mentioned expression (B4) may be arbitrarily determined. In this example, based on the non-patent document 4, the parameters are defined as follows.

In the first potential R1,
ε=0.0951 kcal/mol,
σ=3.473 Å and
$r_c$=8.68 Å.
In the second potential R2,
ε=0.0152 kcal/mol,
σ=2.846 Å and
$r_c$=7.12 Å.
In the third potential R3,
ε=0.0381 kcal/mol,
σ=3.160 Å and
$r_c$=7.90 Å.

Such polymer model 2 can be produced by utilizing an application software J-OCTA created by JSOL corporation for example.

In the second embodiment, since the other processes S2-S12 are the basically same as described above, the duplicate description will be omitted.

In connection with the process S4, when the polymer model 2 is such all-atom model, the number of the polymer models 2 dispose in the space 7 can be set in a range of from about 10 to about 1,000.

In connection with the process S5, when the polymer model 2 is the all-atom model, the interactive potential T includes a first interactive potential T1 between a carbon model 3c and a filler model 11, and a second interactive potential between a hydrogen model 3H and a filler model 11.

The parameters of the interactive potential T1, T2 may be arbitrarily determined. In this example, the parameters are defined as follows.

In the first interactive potential T1,
$\rho_{wall}$=1.0,
$\sigma_{wall}$=3.473 Å,
$\epsilon_{wall}$=0.0951 kcal/mol and
$r_c$=8.68 Å.
In the second interactive potential T2,
$\rho_{wall}$=1.0,
$\sigma_{wall}$=3.160 Å,
$\epsilon_{wall}$=0.0381 kcal/mol and
$r_c$=7.90 Å.

In connection with the relaxation modulus calculation process S82, when the polymer model 2 is the all-atom model, the computing time for the relaxation modulus G(t) using the above-mentioned expression (4) is preferably set in a range of from about 1 nanosecond to about 1 microsecond.

Figure 21:
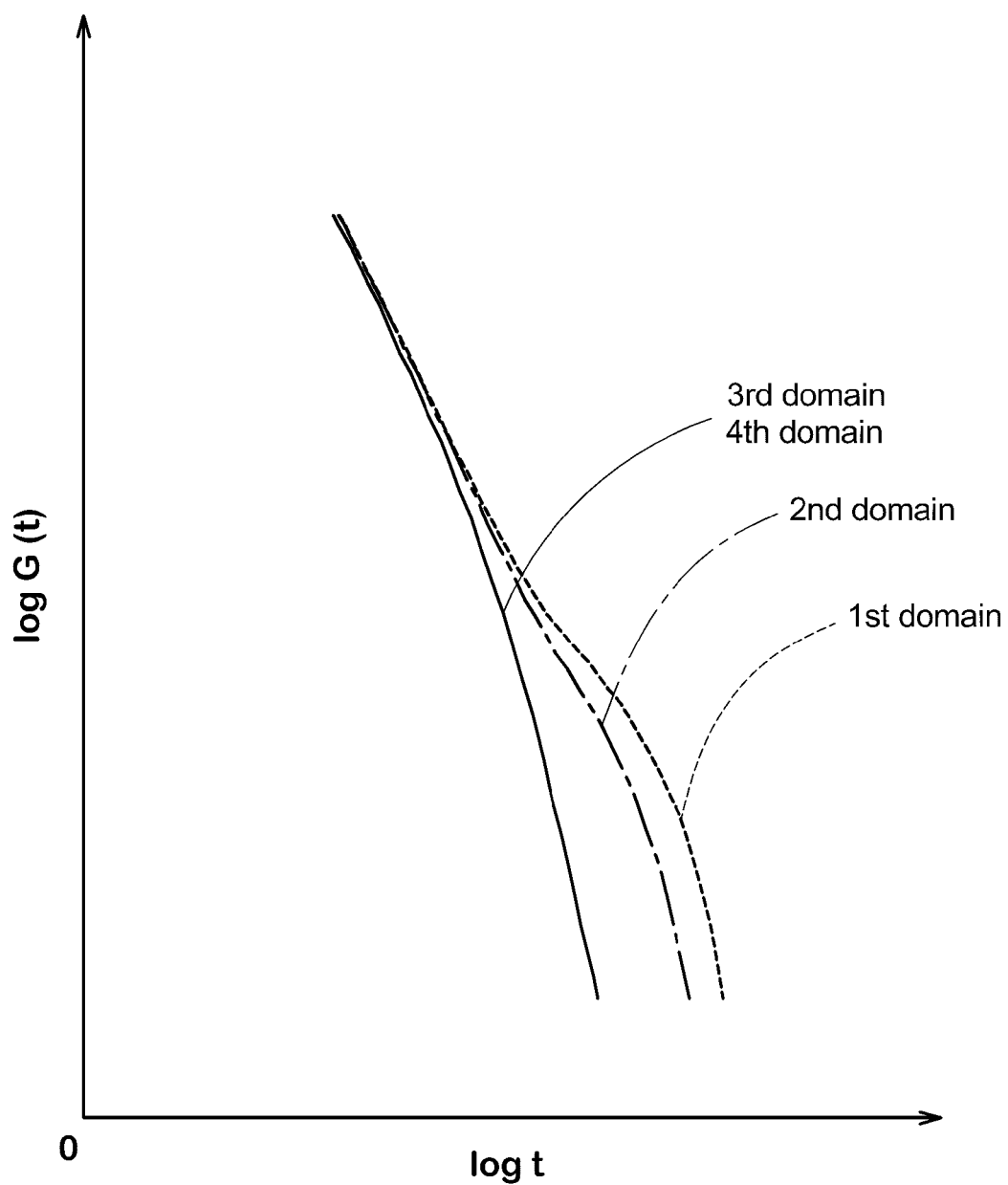
FIG. 21 is a graph showing another example of the relaxation moduli G(t) of first to fourth domains when the polymer models are all-atom models.

FIG. 21 shows an example of the relation between the natural logarithm log G(t) of each of the relaxation moduli G(t) of the first-fourth domains 16A-16D counted from one of the filler models (11A), and the natural logarithm of the time span t when the polymer model 2 is the all-atom model.

Form this graph, it can be seen that the relaxation moduli G(t) of the third domain 16c is the substantially same as that of the fourth domain 16D, the third domain 16c and subsequent domains 16D—are determined as the bulk 14b. The first-second domains 16A-16B are determined as the interface layer 14a.

In connection with the process S84, the equilibrium length $r_0$ of the coupling potential $U_{bond}(r)$ can be set to the distances L4 between the particle models 3. Thereby, the force between the particle models 3 due to the coupling potential $U_{bond}(r)$ becomes zero.

In the case that the polymer model 2 is the all-atom model, it is possible to approximate motions of the polymer models to actual molecular motions of the macromolecular material. Therefore, the initial arrangement of the polymer models 2 can be relaxed with accuracy.

Further, it is possible to simulate and analysis the effects of the monomer configuration, cis configuration or trans configuration of the macromolecular chain, on the thickness of the interface layer.

Figure 22:
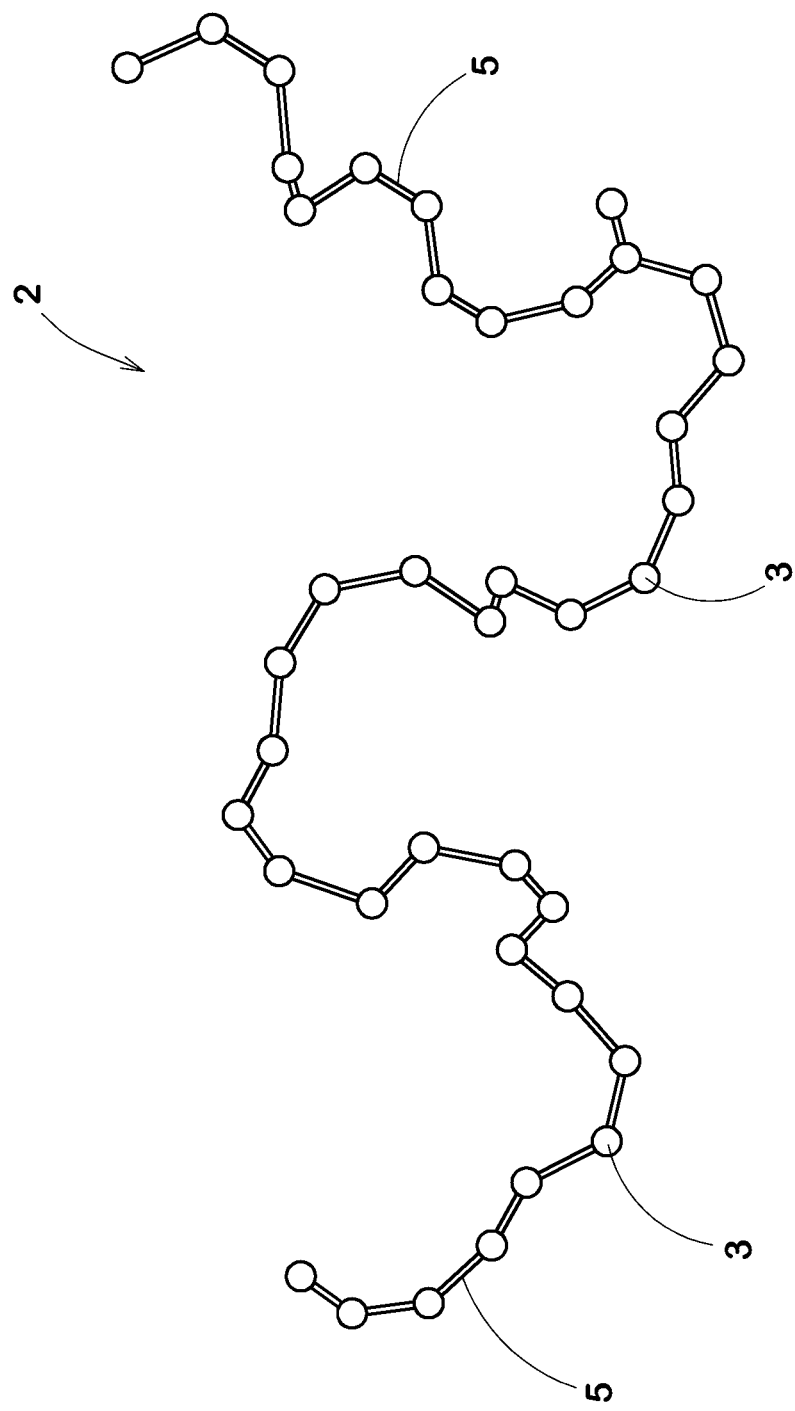
FIG. 22 is a diagram for explaining a united-atom model as a polymer model.

Further, as the third embodiment, the polymer model 2 can be a united-atom model in which a carbon atom and a hydrogen atom bond therewith are modeled by a particle model 3 as shown in FIG. 22 for example. By using such united-atom model, the computational time can be reduced because the number of the hydrogen atoms is reduced while retaining the monomer configuration, cis configuration or trans configuration of the macromolecular chain.

Confirmation Tests

With respect to the first embodiment (coarse-grained model 3), the thickness w1 of the interface layer was computed according to the procedure as explained above as Example 1 and Example 2.

EXAMPLE 1

The repulsive force potential R given by the expression (1) was defined. The number of the particle models 3 in a polymer model was 50. The radius of inertia was 2.89σ. The length L1 of one side of the space 7 was 28.9σ. The number of the polymer models 2 disposed in the space 7 was 300. The computed thickness w1 was 8.67σ. This value well coincides with the measured value.

EXAMPLE 2

The repulsive force potential R given by the expression (A1) was defined. The number of the particle models 3 in a polymer model was 20. The radius of inertia was 1.35σ. The length L1 of one side of the space 7 was 13.5σ. The number of the polymer models 2 disposed in the space 7 was 500. The computed thickness w1 was 4.05σ. This value also well coincides with the measured value.

With respect to the second embodiment (all-atom model 3), the thickness w1 of the interface layer was computed according to the procedure as explained above as Example 3.

EXAMPLE 3

The macromolecular material was cis-1,4 polybutadiene. The polymerization degree (n) was 10. The radius of inertia was 2.5 Å. The length L1 of one side of the space 7 was 40 Å. The number of the polymer models 2 disposed in the space 7 was 100.

The computed thickness w1 was 7.5 Å. This value well coincides with the measured value.

In each example, the computed thickness w1 well coincides with the measured value. Further, in the case of the experimental measurement, it takes several hundred hours to obtain the thickness of the interface layer. But, according to the present invention, it takes only about 1/10 to 1/20 of that time for the computer of a workstation class to compute the thickness w1.

The invention claimed is:

1. A computer-implemented simulation method for a macromolecular material and filler, comprising:
a process in which a polymer model of a macromolecular chain of the macromolecular material modeled by a plurality of particle models is defined;

a process in which a filler model of at least an outer surface of the filler is defined;

a simulation process in which a molecular dynamics calculation is performed using the filler model and the polymer models disposed in a space;

an interface-layer-thickness calculation process in which, the thickness of an interface layer formed between the filler and the bulk of the macromolecular material and having a dynamic property different than that of the bulk, is computed from results of the simulation process, wherein the interface-layer-thickness calculation process comprises a process in which the space in which the polymer models are disposed is partitioned into a plurality of domains bounded by boundary surfaces along said outer surface of the filler, a relaxation modulus calculation process in which relaxation moduli of the domains are computed, and a determining process in which the thickness of the interface layer is computed based on a variation of the relaxation moduli of the domains;

a material property calculation process in which a material property of the macromolecular material with the filler is computed by defining conditions including the computed thickness of the interface layer on the space in which the polymer models are disposed; and a material property judging process in which it is judged whether the computed material property is within an allowable range or not, wherein if the computed material property is outside the allowable range, the conditions defined on the space are changed, and the simulation process, the interface-layer-thickness calculation process, the material property calculation process and the material property judging process are repeated, and if the computed material property is within the allowable range, the macromolecular material with the filler is manufactured based on the conditions defined on the space in which the polymer models are disposed.

2. The method according to claim 1, wherein in the determining process, the relaxation moduli are checked whether or not the difference in the relaxation modulus between every two of the adjacent domains is within a predetermined range, and the domains of which difference is within the predetermined range are determined as being the bulk and the rest are determined as being the interface layer.

3. The method according to claim 1, wherein the space is defined as having a plane forming an outer surface thereof, the filler model is defined by the plane, and the boundary surfaces are defined as being parallel with the filler model.

4. The method according to claim 1, wherein the space is defined as having a pair of oppositely opposed planes forming an outer surface thereof, the filler model is defined by each of the planes, and the boundary surfaces and the filler models are defined as being parallel with each other.

5. The method according to claim 4, wherein the polymer models are disposed between a pair of the filler models.

6. The method according to claim 4, wherein the distance between said oppositely opposed planes is set to be not less than two times the radius of inertia of the polymer model.

7. The method according to claim 4, wherein the distances between the boundary surfaces are defined based on the radius of inertia of the polymer mode.

8. The method according to claim 4, wherein in the relaxation modulus calculation process, each pair of a domain at a distance from one of the two filler models and a domain at the same distance from the other filler model are computed together for a value of the relaxation modulus.

9. The method according to claim 1, wherein the interface-layer-thickness calculation process includes a process in which, prior to the relaxation modulus calculation process, an identical value is assigned with the distances between the particle models of each polymer model.

10. The method according to claim 1, wherein the polymer model is an all-atom model or a united-atom model of the macromolecular chain.

11. The method according to claim 1, wherein the polymer model is a coarse-grained model of the macromolecular chain modeled by a plurality of beads and the particle models are the beads, and a potential between two particle models which can exert a repulsive force between the particle models which increases to infinity as the distance between the particle models decreases, is defined between the particle models of the polymer models.

12. The method according to claim 11, wherein the potential is given by the following expression $$R = \begin{cases} 4\varepsilon\left(\left(\frac{\sigma}{r_{ij}}\right)^{12} - \left(\frac{\sigma}{r_{ij}}\right)^{6} + \frac{1}{4}\right) & \text{if } r_{ij} < 2^{\frac{1}{6}}\sigma \\ 0 & \text{if } r_{ij} \geq 2^{\frac{1}{6}}\sigma \end{cases}$$

wherein $r_{ij}$ is the distance between two beads, $\epsilon$ is a coefficient relating to the intensity of the repulsive force potential R, and $\sigma$ a is a coefficient relating to the distance within which the repulsive force potential R exerts.

13. The method according to claim 1, wherein the polymer model is a coarse-grained model of the macromolecular chain modeled by a plurality of beads and the particle models are the beads, and a repulsive force potential between two particle models which can exert a repulsive force between the particle models which increases up to a finite value as the distance between the particle models decreases, is defined between the particle models of the polymer models.

14. The method according to claim 13, wherein the repulsive force potential is given by the following expression:

$$R = \begin{cases} \frac{1}{2}\left[a_{ij}\left(1 - \frac{r_{ij}}{r_c}\right)^{2}\right] & \text{if } r_{ij} < r_c \\ 0 & \text{if } r_{ij} \geq r_c \end{cases}$$

wherein $r_{ij}$ is the distance between the particle models, $a_{ij}$ is a coefficient relating to the intensity of the repulsive force, and $r_c$ is a cutoff distance.

15. The method according to claim 2, wherein
the space is defined as having a plane forming an outer surface thereof, the filler model is defined by the plane, and
the boundary surfaces are defined as being parallel with the filler model.

16. The method according to claim 2, wherein
the space is defined as having a pair of oppositely opposed planes forming an outer surface thereof, the filler model is defined by each of the planes, and the boundary surfaces and the filler models are defined as being parallel with each other.

17. The method according to claim 5, wherein
the distance between said oppositely opposed planes is set to be not less than two times the radius of inertia of the polymer model.

18. The method according to claim 5, wherein
the distances between the boundary surfaces are defined based on the radius of inertia of the polymer mode.

19. The method according to claim 6, wherein
the distances between the boundary surfaces are defined based on the radius of inertia of the polymer mode.

20. The method according to claim 5, wherein
in the relaxation modulus calculation process, each pair of a domain at a distance from one of the two filler models and a domain at the same distance from the other filler model are computed together for a value of the relaxation modulus.

* * * * *